United States Patent
Aladahalli et al.

(10) Patent No.: US 12,431,237 B2
(45) Date of Patent: Sep. 30, 2025

(54) TASK-SPECIFIC IMAGE STYLE TRANSFER

(71) Applicant: GE Precision Healthcare LLC, Wauwatosa, WI (US)

(72) Inventors: Chandan Kumar Mallappa Aladahalli, Bengaluru (IN); Krishna Seetharam Shriram, Bengaluru (IN); Vikram Reddy Melapudi, Bangalore (IN); Shital Sheshrao Yelne, Nagpur (IN)

(73) Assignee: GE Precision Healthcare LLC, Waukesha, WI (US)

( * ) Notice: Subject to any disclaimer, the term of this patent is extended or adjusted under 35 U.S.C. 154(b) by 387 days.

(21) Appl. No.: 18/149,485

(22) Filed: Jan. 3, 2023

(65) Prior Publication Data

US 2024/0221912 A1    Jul. 4, 2024

(51) Int. Cl.
*G06T 7/00* (2017.01)
*G06V 10/54* (2022.01)
*G06V 10/771* (2022.01)
*G06V 10/82* (2022.01)
*G16H 30/40* (2018.01)

(52) U.S. Cl.
CPC .......... *G16H 30/40* (2018.01); *G06T 7/0012* (2013.01); *G06V 10/54* (2022.01); *G06V 10/771* (2022.01); *G06V 10/82* (2022.01); *G06T 2207/10132* (2013.01); *G06T 2207/20084* (2013.01)

(58) Field of Classification Search
CPC ................. G16H 30/40; G06T 7/0012; G06T 2207/10132; G06T 2207/20084; G06V 10/54; G06V 10/771; G06V 10/82; A61B 6/5205; A61B 8/461; A61B 8/5207; A61B 6/461
See application file for complete search history.

(56) References Cited

U.S. PATENT DOCUMENTS

2020/0202502 A1*  6/2020  Tsymbalenko ............ G06T 5/60
2021/0182687 A1*  6/2021  Son ........................ G06F 18/22
(Continued)

OTHER PUBLICATIONS

Liu, Zh. et al. | "Remove Appearance Shift for Ultrasound Image Segmentation Via Fast and Universal Style Transfer." arXiv:2002.05844v1 [eess.IV] Feb. 14, 2020, 5 pages.
(Continued)

*Primary Examiner* — John Villecco
*Assistant Examiner* — Han Hoang
(74) *Attorney, Agent, or Firm* — Amin, Turocy & Watson, LLP

(57) ABSTRACT

Systems/techniques that facilitate task-specific image style transfer are provided. In various embodiments, a system can access a first medical image, wherein the first medical image can exhibit anatomical content and a first visual style. In various aspects, the system can generate, via execution of an optimization algorithm, a second medical image based on the first medical image, wherein the second medical image can exhibit the anatomical content and a second visual style that is different from the first visual style. In various instances, the optimization algorithm can be based on feature maps extracted from a pre-trained deep learning neural network that has been configured to perform an inferencing task on medical images exhibiting the second visual style.

20 Claims, 19 Drawing Sheets

(56) References Cited

U.S. PATENT DOCUMENTS

2021/0233239 A1* 7/2021 Li .......................... G16H 30/40
2022/0020191 A1* 1/2022 Lin .......................... G06T 11/60

OTHER PUBLICATIONS

Liu, Zh. et al. | "Generalize Ultrasound Image Segmentation via Instant and Plug & Play Style Transfer." arXiv: 2101.03711v1 [eess.IV] Jan. 11, 2021, 5 pages.
Gatys, L. A et al. | "Image Style Transfer Using Convolutional Neural Networks." 2016 IEEE Conference on Computer Vision and Pattern Recognition (CVPR), 2016, pp. 2414-2423, doi: 10.1109/CVPR.2016.265, 10 pages.
Keras | "SGD", webpage https://keras.io/api/optimizers/sgd/, last accessed Dec. 23, 2022, 2 pages.
Tensorflow | "tfp.optimizer.bfgs_minimize", wepbage https://www.tensorflow.org/probability/api_docs/python/tfp/optimizer/bfgs_minimize, last accessed Dec. 23, 2022, 5 pages.

* cited by examiner

TASK-SPECIFIC IMAGE STYLE TRANSFER

TECHNICAL FIELD

The subject disclosure relates generally to image style transfer, and more specifically to task-specific image style transfer.

BACKGROUND

A deep learning neural network can be trained to perform an inferencing task on a given medical image. How accurately the deep learning neural network performs the inferencing task can depend upon whether a visual style or texture exhibited by the given medical image matches visual styles or textures exhibited by medical images on which the deep learning neural network was trained. If the deep learning neural network was not trained on the visual style or texture exhibited by the given medical image, then the deep learning neural network cannot be expected to accurately or reliably perform the inferencing task on the given medical image. In other words, the deep learning neural network can be considered as having a diminished generalizability. Various existing techniques address this issue by first performing a style-transfer on the given medical image, and then subsequently executing the deep learning neural network on the style-transferred version of the given medical image. In particular, such existing techniques train a separate neural network to perform style-transfer, where such training is conducted in supervised fashion using voluminous amounts of paired training data. Unfortunately, it is often impractical or infeasible to obtain such voluminous amounts of paired training data in real-world clinical settings.

Accordingly, systems or techniques that can facilitate style-transfer in the absence of voluminous amounts of paired training data can be considered as desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate task-specific image style transfer are described.

According to one or more embodiments, a system is provided. The system can comprise a non-transitory computer-readable memory that can store computer-executable components. The system can further comprise a processor that can be operably coupled to the non-transitory computer-readable memory and that can execute the computer-executable components stored in the non-transitory computer-readable memory. In various embodiments, the computer-executable components can comprise an access component that can access a first medical image, wherein the first medical image can exhibit anatomical content and a first visual style. In various aspects, the computer-executable components can comprise a style-transfer component that can generate, via execution of an optimization algorithm, a second medical image based on the first medical image, wherein the second medical image can exhibit the anatomical content and a second visual style that is different from the first visual style. In various instances, the optimization algorithm can be based on feature maps extracted from a pre-trained deep learning neural network that has been configured to perform an inferencing task on medical images exhibiting the second visual style.

According to one or more embodiments described herein, a computer-implemented method is provided. In various embodiments, the computer-implemented method can comprise accessing, by a device operatively coupled to a processor, a first medical image, wherein the first medical image can exhibit anatomical content and a first visual style. In various aspects, the computer-implemented method can comprise generating, by the device and via execution of an optimization algorithm, a second medical image based on the first medical image, wherein the second medical image can exhibit the anatomical content and a second visual style that is different from the first visual style. In various instances, the optimization algorithm can be based on feature maps extracted from a pre-trained deep learning neural network that has been configured to perform an inferencing task on medical images exhibiting the second visual style.

According to one or more embodiments, a computer program product for facilitating task-specific image style transfer is provided. In various embodiments, the computer program product can comprise a non-transitory computer-readable memory having program instructions embodied therewith. In various aspects, the program instructions can be executable by a processor to cause the processor to access a medical image exhibiting a visual texture. In various instances, the program instructions can be executable by the processor to cause the processor to iteratively execute an optimization algorithm on the medical image, thereby yielding a style-transferred version of the medical image that exhibits a different visual texture. In various cases, the optimization algorithm can be based on hidden layer activations extracted from a neural network, wherein the neural network can have been pre-trained to operate on medical images exhibiting the different visual texture. In various aspects, the program instructions can be executable by the processor to cause the processor to execute the neural network on the style-transferred version of the medical image.

DETAILED DESCRIPTION

Figure 1:
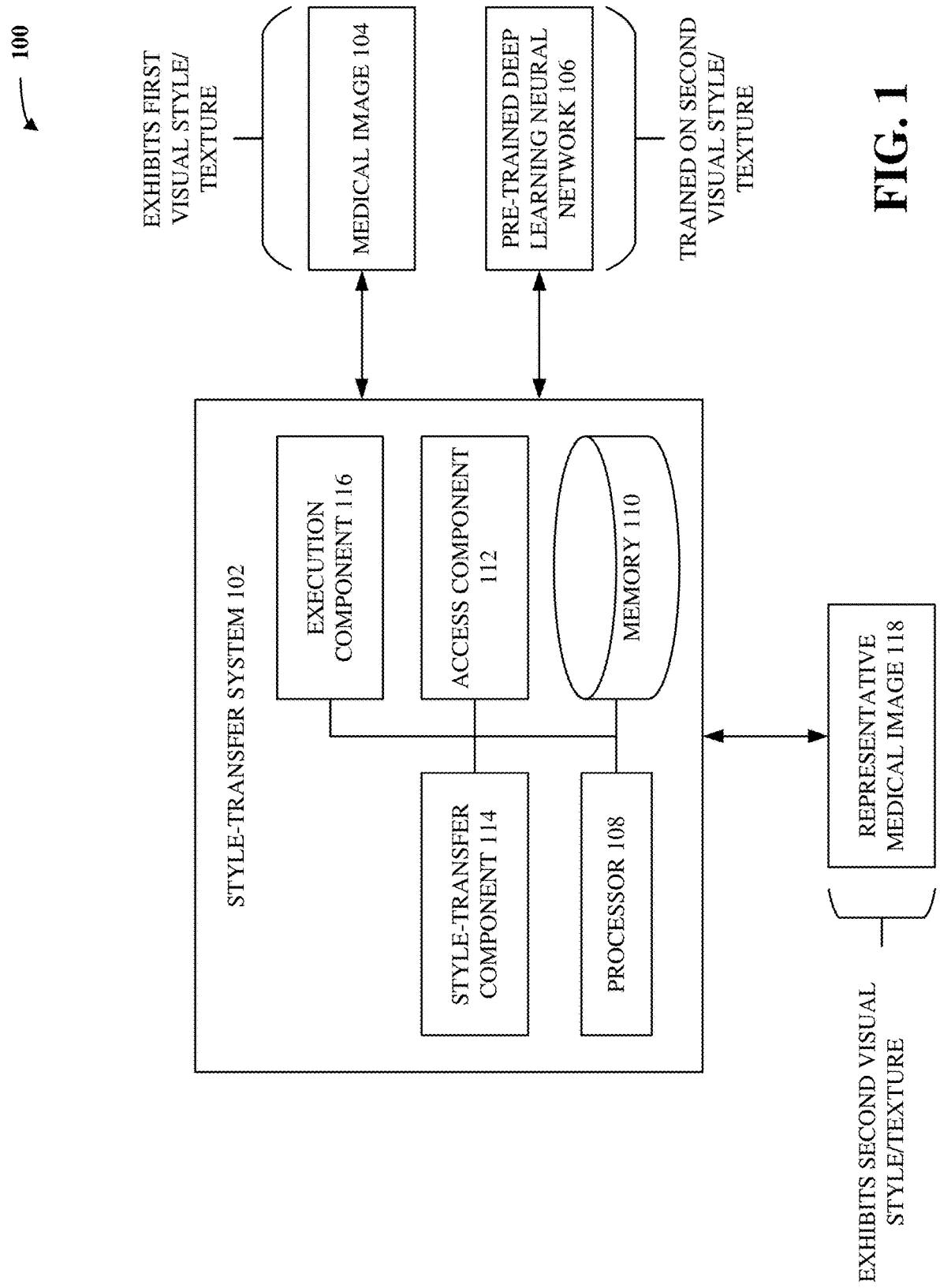
FIG. 1 illustrates a block diagram of an example, non-limiting system that facilitates task-specific image style transfer in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A deep learning neural network can be trained to perform an inferencing task (e.g., image classification, image segmentation, image regression) on a given medical image (e.g., a given computed tomography (CT) scanned image, a given magnetic resonance imaging (MRI) scanned image, a given positron emission tomography (PET) scanned image, a given X-ray scanned image, a given ultrasound scanned image).

Regardless of whichever medical imaging modality (e.g., CT scanner, MRI scanner, PET scanner, X-ray scanner, ultrasound scanner) is implemented to capture or generate the given medical image, the given medical image can be considered as conveying at least two distinct types of visual information. One distinct type of visual information conveyed by the given medical image can be anatomical content. The anatomical content of the given medical image can be or otherwise include whatever anatomical structures (e.g., brain, teeth, lungs, colon, spine, muscle tissue, bone tissue, blood vessels) are collectively depicted or illustrated by the pixels or voxels of the given medical image. Another distinct type of visual information conveyed by the given medical image can be style or texture. The style or texture of the given medical image can be or otherwise include one or more perceived visual characteristics or qualities (e.g., brightness, contrast, blurriness, noise, resolution, shading, optical distortions) according to which the given medical image depicts or illustrates the anatomical content. In other words, the anatomical content can be considered as being what the given medical image depicts, and the style or texture can be considered as being how the given medical image depicts it.

Note that style or texture can depend upon or otherwise be a function of medical imaging modality. For instance, medical images that are generated or captured by a particular medical imaging modality (e.g., ultrasound scanner) can exhibit a particular style or texture, whereas medical images that are generated or captured by a different medical imaging modality (e.g., CT scanner) can exhibit a different style or texture. Furthermore, note that style or texture can depend upon or otherwise be a function of configurable settings of a medical imaging modality. For instance, medical images that are generated or captured by a specific medical imaging modality (e.g., by a specific ultrasound scanner) can exhibit a particular style or texture when the specific medical imaging modality is operated with a particular settings configuration (e.g., particular voltage, particular amperage, particular display field of view, particular scan speed, particular focal spot size), whereas medical images that are generated or captured by that same specific medical imaging modality (e.g., by that same specific ultrasound scanner) can exhibit a different style or texture when that same specific medical imaging modality is operated with a different settings configuration (e.g., different voltage, different amperage, different display field of view, different scan speed, different focal spot size). Further still, note that style or texture can depend upon or otherwise be a function of non-configurable characteristics that are unique to an instantiation of a medical imaging modality. For instance, medical images that are generated or captured by a particular instantiation of a medical imaging modality (e.g., by a particular CT scanner) can exhibit a specific style or texture due to various inherent characteristics that are unique to that particular instantiation of the medical imaging modality (e.g., due to a unique bias field experienced by that particular CT scanner, due to a unique intra-scan focal spot displacement pattern experienced by that particular CT scanner), whereas medical images that are generated or captured by a different instantiation of that same medical imaging modality (e.g., by a different CT scanner) can exhibit a different style or texture due to various inherent characteristics that are unique to that different instantiation of that same medical imaging modality (e.g., due to a unique bias field experienced by that different CT scanner, due to a unique intra-scan focal spot displacement pattern experienced by that different CT scanner).

In any case, how accurately or how inaccurately the deep learning neural network performs the inferencing task on the given medical image can depend upon whether or not the visual style or texture that is exhibited by the given medical image matches whatever visual styles or textures were exhibited by medical images on which the deep learning neural network was trained. For example, suppose that the style or texture of the given medical image matches that of the medical images on which the deep learning neural network was trained. This can occur when the given medical image is generated or captured by the same medical imaging modality operating at the same settings configuration that was used to generate or capture the medical images on which the deep learning neural network was trained. In such case, the deep learning neural network can be expected to correctly, accurately, or otherwise reliably perform the inferencing task on the given medical image, due to such style/texture match. In contrast, suppose that the style or texture of the given medical image does not match that of the medical images on which the deep learning neural network was trained. In some instances, this can occur when the given medical image is generated or captured by the same medical imaging modality operating at a different settings configuration than was used to generate or capture the medical images on which the deep learning neural network was trained. In other instances, this can occur when the given medical image is generated or captured by a different medical imaging modality altogether than was used to generate or capture the medical images on which the deep learning neural network was trained. In either case, the deep learning neural network cannot be expected to correctly, accurately, or otherwise reliably perform the inferencing task on the given medical image, due to such style/texture mismatch.

Accordingly, because the deep learning neural network can be expected to perform the inferencing task properly only on medical images that exhibit the same style or texture on which the deep learning neural network was trained, the deep learning neural network can be considered as having a limited, diminished, reduced, or otherwise restricted generalizability.

Various existing techniques address this reduced generalizability by performing a style-transfer prior to executing the deep learning neural network. More specifically, suppose that the style or texture of the given medical image does not match that on which the deep learning neural network was trained. In such case, such existing techniques first execute a style-transfer neural network on the given medical image, thereby yielding a style-transferred version of the given medical image, where such style-transferred version depicts the same anatomical content as the given medical image, but where such style-transferred version exhibits the style or texture on which the deep learning neural network was trained. Such existing techniques then execute the deep learning neural network on the style-transferred version of the given medical image. In this way, the inferencing task can be performed on or otherwise with respect to the anatomical content illustrated by the given medical image, without being hampered by the style/texture mismatch between the given medical image and the medical images on which the deep learning neural network was trained.

Note that such existing techniques generally train the style-transfer neural network in a supervised fashion using voluminous amounts of paired training data. In particular, such paired training data includes a large number of medical images exhibiting the same style or texture as the given medical image, and the paired training data also includes a respective ground-truth style-transferred version of each of such large number of medical images, where such ground-truth style-transferred version exhibits the style or texture on which the deep learning neural network was trained.

Unfortunately, it is often impractical, infeasible, or otherwise difficult to obtain such voluminous amounts of paired training data. Indeed, such existing techniques usually create such voluminous amounts of paired training data by performing double-scans of medical patients. In particular, for any given medical patient, such existing techniques generate or capture a first medical image by scanning that medical patient with whatever medical imaging modality was used to create the medical images on which the deep learning neural network was trained, and such existing techniques generate or capture a second medical image by scanning that same medical patient using a different medical imaging modality or by using the same medical imaging modality with a different settings configuration. Accordingly, the first medical image can be considered as a ground-truth style-transferred version of the second medical image.

However, such double-scanning suffers from various problems, such as registration issues and radiation exposure concerns. More specifically, although the first medical image and the second medical image can depict the same medical patient, they can be misregistered (e.g., misaligned) with each other (e.g., the medical patient, due to breathing or postural changes, might have been in different bodily positions or orientations when the first and second medical images were being captured or generated). Additionally, because the first medical image and the second medical image are generated or captured from the same medical patient, that medical patient can have been exposed to heightened or excessive amounts of radiation, which can potentially have negative health consequences.

Accordingly, systems or techniques that can facilitate style-transfer in the absence of voluminous amounts of paired training data can be considered as desirable.

Various embodiments described herein can address one or more of these technical problems. One or more embodiments described herein include systems, computer-implemented methods, apparatus, or computer program products that can facilitate task-specific image style transfer. More specifically, the inventors of various embodiments described herein devised various techniques for performing image style transfer, which various techniques do not involve obtaining voluminous amounts of paired training data. More specifically still, the present inventors realized that such voluminous amounts of paired training data can be eliminated by instead utilizing, at inference time, feature maps or activation maps generated by hidden layers of the deep learning neural network that is configured to perform the inferencing task. Because such feature maps or activation maps can be obtained without performing double-scans on medical patients, various embodiments described herein can avoid the above-mentioned problems of misregistration and excessive radiation exposure. Moreover, because style-transfer as described herein can be based on the feature maps or activation maps generated by hidden layers of the deep learning neural network, and because the deep learning neural network can be pre-trained to perform the inferencing task, various embodiments described herein can be considered as performing image style-transfer in a fashion that is tailored to, tied to, or otherwise specific to the inferencing task (hence the term "task-specific").

Various embodiments described herein can be considered as a computerized tool (e.g., any suitable combination of computer-executable hardware or computer-executable software) that can facilitate task-specific image style transfer. In various aspects, such computerized tool can comprise an access component, a style-transfer component, or an execution component.

In various embodiments, there can be a medical image. In various aspects, the medical image can depict any suitable anatomical content. That is, the medical image can illustrate one or more anatomical structures (e.g., tissues, organs, body parts, or portions thereof) of a medical patient (e.g., human, animal, or otherwise). In various instances, the medical image can exhibit any suitable size, format, or dimensionality (e.g., can be a two-dimensional pixel array, can be a three-dimensional voxel array). In various cases, the medical image can be generated or otherwise captured by any suitable medical imaging modality (e.g., by a CT scanner, by an MRI scanner, by an X-ray scanner, by a PET scanner, or by an ultrasound scanner). In various aspects, the medical image can have undergone any suitable image reconstruction technique (e.g., filtered back projection).

In any case, the medical image can be considered as exhibiting a first style or texture. In various instances, the first style or texture can depend upon the medical imaging modality that generated or captured the medical image (e.g., can depend upon configurable settings or controls of the medical imaging modality, can depend upon non-configurable characteristics inherent to the medical imaging modality).

In various embodiments, there can be a pre-trained neural network. In various instances, the pre-trained neural network can exhibit any suitable internal architecture. For example, the pre-trained neural network can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the pre-trained neural network can include any suitable numbers of neurons in various layers (e.g., different layers can have the same or different numbers of neurons as each other). As yet another example, the pre-trained neural network can include any suitable activation functions (e.g., softmax, sigmoid, hyperbolic tangent, rectified linear unit) in various neurons (e.g., different neurons can have the same or different activation functions as each other). As still another example, the pre-trained neural network can include any suitable interneuron connections or interlayer connections (e.g., forward connections, skip connections, recurrent connections).

In various aspects, the pre-trained neural network can have been trained in any suitable fashion (e.g., via supervised training, via unsupervised training, via reinforcement learning) to perform any suitable inferencing task on inputted medical images, which inputted medical images can have the same size, format, or dimensionality as the medical image mentioned above. As some non-limiting examples, the inferencing task can be image classification (e.g., producing a classification label for an inputted medical image), image segmentation (e.g., producing a pixel-wise or voxel-wise segmentation mask for an inputted medical image), or image regression (e.g., producing a denoised, resolution-enhanced, or compressed version of an inputted medical image).

In various instances, the pre-trained neural network can have been trained on a second style or texture that is different from (e.g., that does not match) the first style or texture of the medical image mentioned above. In other words, the pre-trained neural network can have encountered any suitable number of medical images during its training, and such medical images can each have exhibited the second style or texture rather than the first style or texture. As an example, those medical images on which the pre-trained neural network was trained can have been captured or generated by a different medical imaging modality than was used to capture or generate the medical image mentioned above. As another example, those medical images on which the pre-trained neural network was trained can have been captured or generated by the same medical imaging modality as was used to capture or generate the medical image mentioned above, but such medical imaging modality can have been operated according to a different settings configuration.

In various embodiments, there can be another medical image that can be considered as being representative of those medical images on which the pre-trained neural network was trained. For case of explanation, this can be referred to as a representative medical image. In various instances, the representative medical image can have the same size, format, or dimensionality (e.g., the same number or arrangement of pixels or voxels) as the medical image discussed above. For example, if the medical image is a two-dimensional pixel array, then the representative medical image can likewise be a two-dimensional pixel array having the same number of pixel rows and pixel columns as the medical image. As another example, if the medical image is a three-dimensional voxel array, then the representative medical image can likewise be a three-dimensional voxel array having the same number of voxel rows, voxel columns, and voxel layers as the medical image. In various cases, the representative medical image can exhibit its own unique anatomical content (e.g., can depict or illustrate any suitable anatomical structures of any suitable medical patient). In various aspects, the representative medical image can exhibit the second style or texture, rather than the first style or texture. In some instances, this can be accomplished by capturing or generating the representative medical image with the same medical imaging modality operating at the same settings configuration as was used to capture or generate the medical images on which the pre-trained neural network was trained. Indeed, in some cases, the representative medical image can be a medical image that the pre-trained neural network encountered during training.

In any case, it can be desired to perform the inferencing task on the medical image. However, because the medical image can exhibit the first style or texture, and because the pre-trained neural network can have been trained on the second style or texture, the pre-trained neural network cannot be expected to reliably, accurately, or correctly perform the inferencing task on the medical image. In various aspects, the computerized tool described herein can generate, without utilizing voluminous amounts of paired training data, a style-transferred version of the medical image, where such style-transferred version can exhibit the second style or texture rather than the first style or texture. The pre-trained neural network can accordingly be executed on such style-transferred version.

In various embodiments, the access component of the computerized tool can electronically receive or otherwise electronically access the medical image, the pre-trained neural network, or the representative medical image. In some aspects, the access component can electronically retrieve the medical image, the pre-trained neural network, or the representative medical image from any suitable centralized or decentralized data structures (e.g., graph data structures, relational data structures, hybrid data structures), whether remote from or local to the access component. In any case, the access component can electronically obtain or access the medical image, the pre-trained neural network, or the representative medical image, such that other components of the computerized tool can electronically interact with (e.g., read, write, edit, copy, manipulate) the medical image, the pre-trained neural network, or the representative medical image.

In various embodiments, the style-transfer component of the computerized tool can electronically store, maintain, control, or otherwise access an in-situ style-transfer optimization algorithm. In various aspects, the in-situ style-transfer optimization algorithm can be any suitable algorithm (e.g., any suitable defined sequence of mathematical operations, such as a stochastic gradient descent algorithm or a Broyden-Fletcher-Goldfarb-Shanno algorithm) that can indicate how the values of one or more independent variables should be updated or changed so as to mathematically minimize (e.g., so as to optimize) any suitable objective function that depends upon those one or more independent variables. In various instances, as described herein, the one or more independent variables can be pixel values or voxels values of the medical image, and the objective function can be any suitable mathematical function or combination of mathematical functions that can take as arguments feature maps or activation maps which can be generated by hidden layers of the pre-trained neural network based on the medical image and which can also take as arguments other feature maps or activation maps which can be generated by the hidden layers based on the representative medical image. In various cases, as described herein, the style-transfer component can iteratively execute or otherwise perform the in-situ style-transfer optimization algorithm on the medical image, and such iterative execution can cause the style-transfer component to update or otherwise change the pixel values or voxel values of the medical image at each iteration, so as to minimize the objective function. After completion of all iterations (e.g., when any suitable optimization termination criterion is achieved), the end-result can be a style-transferred medical image.

In various aspects, the style-transferred medical image can have the same size, format, or dimensionality as the medical image itself. As an example, if the medical image is a two-dimensional pixel array, then the style-transferred medical image can likewise be a two-dimensional pixel array having the same number of pixel rows and pixel columns as the medical image. As another example, if the medical image is a three-dimensional voxel array, then the style-transferred medical image can likewise be a three-dimensional voxel array having the same number of voxel rows, voxel columns, and voxel layers as the medical image. In various instances, the style-transferred medical image can have the same anatomical content as the medical image. That is, the pixels or voxels of the style-transferred medical image can collectively visually depict or illustrate the same anatomical structures as the pixels or voxels of the medical image. However, in various cases, the style-transferred medical image can exhibit the second style or texture, instead of the first style or texture. Accordingly, the style-transferred medical image can be considered as a transformed version of the medical image, which transformed version exhibits the same anatomical content as the medical image but a different style/texture than the medical image.

In various embodiments, the execution component of the computerized tool can electronically execute the pre-trained neural network on the style-transferred medical image, thereby yielding an inferencing task result. More specifically, the execution component can feed the style-transferred medical image to an input layer of the pre-trained neural network, the style-transferred medical image can complete a forward pass through one or more hidden layers of the pre-trained neural network, and an output layer of the pre-trained neural network can compute the inferencing task result based on activations generated by the one or more hidden layers of the pre-trained neural network.

In various aspects, the inferencing task result can be any suitable electronic data exhibiting any suitable size, format, or dimensionality (e.g., can be one or more scalars, one or more vectors, one or more matrices, one or more tensors, or one or more character strings) corresponding to the inferencing task. For example, if the inferencing task is image classification, then the inferencing task result can be a classification label that the pre-trained neural network has generated for the style-transferred medical image. As another example, if the inferencing task is image segmentation, then the inferencing task result can be a pixel-wise or voxel-wise segmentation mask that the pre-trained neural network has generated for the style-transferred medical image. As yet another example, if the inferencing task is image regression, then the inferencing task result can be a continuously-variable regression output that the pre-trained neural network has generated for the style-transferred medical image (e.g., can be a denoised version of the style-transferred medical image, can be resolution-enhanced version of the style-transferred medical image, can be a latent vector representing the style-transferred medical image).

In any case, because the pre-trained neural network can have been trained on the second style or texture, and because the style-transferred medical image can exhibit the second style or texture, the inferencing task result can exhibit a heightened level of accuracy, precision, confidence, or reliability. In other words, the pre-trained neural network can accurately, correctly, or reliably perform the inferencing task on the style-transferred medical image. In stark contrast, because the pre-trained neural network can have been trained on the second style or texture, and because the original version of the medical image can exhibit the first style or texture, the pre-trained neural network cannot be expected to accurately, correctly, or reliably perform the inferencing task on the original version of the medical image.

In various aspects, the execution component can electronically transmit the style-transferred medical image or the inferencing task result to any suitable computing devices. In various instances, the execution component can electronically render the style-transferred medical image or the inferencing task result on any suitable electronic displays (e.g., computer screens, computer monitors, graphical user-interfaces).

Various additional details regarding how the in-situ style-transfer optimization algorithm can be iteratively executed so as to generate the style-transferred medical image are provided below.

In various aspects, the style-transfer component can execute the pre-trained neural network on the representative medical image. In other words, the style-transfer component can feed the representative medical image to the pre-trained neural network, and the representative medical image can complete a forward pass through whatever layers make up the pre-trained neural network.

Note that, in various instances, the pre-trained neural network can comprise one or more shallow layers, and the pre-trained neural network can also comprise one or more deep layers. In various cases, the one or more shallow layers can be considered as being any suitable neural network layers that are positioned near an upstream (e.g., input) end of the pre-trained neural network. In contrast, the one or more deep layers can be considered as being any suitable neural network layers that are positioned downstream of the one or more shallow layers. For example, the one or more shallow layers can include an s-th layer of the pre-trained neural network to a 1-th layer of the pre-trained neural network, and the one or more deep layers can include a u-th layer of the pre-trained neural network to a v-th layer of the pre-trained neural network, for any suitable positive integers $1 \leq s \leq t < u \leq v$. Note that, in various aspects, the one or more shallow layers and the one or more deep layers can be considered as subsets (e.g., strict or not strict) of the total layers that make up the pre-trained neural network. In other words, the pre-trained neural network can include any other suitable neural network layers in addition to the one or more shallow layers and in addition to the one or more deep layers.

In any case, because the one or more shallow layers can be located more upstream in the pre-trained neural network, the one or more shallow layers can be considered as being responsible for analyzing or processing the style or texture of an inputted medical image (or at least can be considered as learning to analyze or process whatever aspects of such style or texture are relevant to performance of the inferencing task). In contrast, because the one or more deep layers can be located more downstream in the pre-trained neural network, the one or more deep layers can be considered as being responsible for analyzing or processing the anatomical content of an inputted medical image (or at least can be considered as learning to analyze or process whatever aspects of such anatomical content are relevant to performance of the inferencing task).

So, as mentioned above, the style-transfer component can execute the pre-trained neural network on the representative medical image. In various aspects, this can cause the pre-trained neural network to produce an inferencing task result corresponding to the representative medical image. For case of explanation, such inferencing task result can be referred to as the inferencing task result A. More specifically, the style-transfer component can feed the representative medical image to an input layer of the pre-trained neural network, the representative medical image can complete a forward pass through one or more hidden layers of the pre-trained neural network, and an output layer of the pre-trained neural network can calculate the inferencing task result A based on activations from the one or more hidden layers of the pre-trained neural network.

Note that, because the pre-trained neural network can comprise the one or more shallow layers and the one or more deep layers mentioned above, the representative medical image can pass through the one or more shallow layers and the one or more deep layers during such forward pass.

In various instances, as the representative medical image passes through the one or more shallow layers, the one or more shallow layers can generate one or more activation maps (also referred to as feature maps) based on the representative medical image. For case of explanation, these can be referred to as the one or more shallow activation maps A. Note that, because the one or more shallow layers can be considered as being responsible for analyzing or processing the style or texture of an inputted medical image, the one or more shallow activation maps A can be considered as representing or otherwise being relevant to the style or texture that is exhibited by the representative medical image: that is, the second style or texture.

Similarly, as the representative medical image passes through the one or more deep layers, the one or more deep layers can generate one or more activation maps (also referred to as feature maps) based on the representative medical image. For case of explanation, these can be referred to as the one or more deep activation maps A. Note that, because the one or more deep layers can be considered as being responsible for analyzing or processing the anatomical content of an inputted medical image, the one or more deep activation maps A can be considered as representing or otherwise being relevant to whatever anatomical content that is exhibited by the representative medical image.

In various cases, the style-transfer component can discard the inferencing task result A and the one or more deep activation maps A. However, in various instances, the style-transfer component can preserve or store the one or more shallow activation maps A.

Now, in various aspects, the style-transfer component can execute the pre-trained neural network on the medical image that exhibits the first style or texture. In various cases, this can cause the pre-trained neural network to produce an inferencing task result corresponding to the medical image. For case of explanation, such inferencing task result can be referred to as the inferencing task result B. In particular, the style-transfer component can feed the medical image to the input layer of the pre-trained neural network, the medical image can complete a forward pass through the one or more hidden layers of the pre-trained neural network, and the output layer of the pre-trained neural network can calculate the inferencing task result B based on activations from the one or more hidden layers of the pre-trained neural network.

Again, note that, because the pre-trained neural network can comprise the one or more shallow layers and the one or more deep layers mentioned above, the medical image can pass through the one or more shallow layers and the one or more deep layers during such forward pass.

In various instances, as the medical image passes through the one or more shallow layers, the one or more shallow layers can generate one or more activation maps based on the medical image. For case of explanation, these can be referred to as the one or more shallow activation maps B. Note that, because the one or more shallow layers can be considered as being responsible for analyzing or processing the style or texture of an inputted medical image, the one or more shallow activation maps B can be considered as representing or otherwise being relevant to the style or texture that is exhibited by the medical image: that is, the first style or texture.

Similarly, as the medical image passes through the one or more deep layers, the one or more deep layers can generate one or more activation maps based on the medical image. For case of explanation, these can be referred to as the one or more deep activation maps B. Note that, because the one or more deep layers can be considered as being responsible for analyzing or processing the anatomical content of an inputted medical image, the one or more deep activation maps B can be considered as representing or otherwise being relevant to whatever anatomical content that is exhibited by the medical image.

In various cases, the style-transfer component can discard the inferencing task result B and the one or more shallow activation maps B. However, in various instances, the style-transfer component can preserve or store the one or more deep activation maps B.

Now, in various aspects, the style-transfer component can iteratively execute the in-situ style-transfer optimization algorithm as follows. During a current iteration of such iterative execution, the style-transfer component can access a previously-updated version of the medical image, where such previously-updated version can have been generated by the in-situ style-transfer optimization algorithm during the immediately previous iteration. Note that, if the current iteration is the first iteration of such iterative execution, then there can be no immediately previous iteration. In such case, the original version of the medical image can be considered or otherwise treated as the previously-updated version of the medical image. In any case, the style-transfer component can execute the pre-trained neural network on the previously-updated version of the medical image. In various aspects, this can cause the pre-trained neural network to produce an inferencing task result corresponding to the previously-updated version of the medical image. For case of explanation, such inferencing task result can be referred to as the inferencing task result C. In particular, the style-transfer component can feed the previously-updated version of the medical image to the input layer of the pre-trained neural network, the previously-updated version of the medical image can complete a forward pass through the one or more hidden layers of the pre-trained neural network, and the output layer of the pre-trained neural network can calculate the inferencing task result C based on activations from the one or more hidden layers of the pre-trained neural network.

Again, note that, because the pre-trained neural network can comprise the one or more shallow layers and the one or more deep layers mentioned above, the previously-updated version of the medical image can pass through the one or more shallow layers and the one or more deep layers during such forward pass.

In various instances, as the previously-updated version of the medical image passes through the one or more shallow layers, the one or more shallow layers can generate one or more activation maps based on the previously-updated version of the medical image. For case of explanation, these can be referred to as the one or more shallow activation maps C. Note that, because the one or more shallow layers can be considered as being responsible for analyzing or processing the style or texture of an inputted medical image, the one or more shallow activation maps C can be considered as representing or otherwise being relevant to whatever style or texture that is exhibited by the previously-updated version of the medical image.

Similarly, as the previously-updated version of the medical image passes through the one or more deep layers, the one or more deep layers can generate one or more activation maps based on the previously-updated version of the medical image. For case of explanation, these can be referred to as the one or more deep activation maps C. Note that, because the one or more deep layers can be considered as being responsible for analyzing or processing the anatomical content of an inputted medical image, the one or more deep activation maps C can be considered as representing or otherwise being relevant to whatever anatomical content that is exhibited by the previously-updated version of the medical image.

In various cases, the style-transfer component can discard the inferencing task result C. However, in various instances, the style-transfer component can preserve or store the one or more shallow activation maps C and the one or more deep activation maps C.

Now, in various aspects, the style-transfer component can compute one or more first errors (e.g., mean absolute error (MAE), mean squared error (MSE), cross-entropy) between: the one or more shallow activation maps A; and the one or more shallow activation maps C. In various instances, because the one or more shallow activation maps A can be considered as representing or otherwise being relevant to the second style or texture, such one or more first errors can be considered as indicating how closely the style or texture of the previously-updated version of the medical image matches the second style or texture. Moreover, in various cases, the style-transfer component can compute one or more second errors (e.g., MAE, MSE, cross-entropy) between: the one or more deep activation maps B; and the one or more deep activation maps C. In various aspects, because the one or more deep activation maps B can be considered as representing or otherwise being relevant to the anatomical content exhibited by the medical image, such one or more second errors can be considered as indicating how closely the anatomical content of the previously-updated version of the medical image matches that of the medical image.

In various aspects, the style-transfer component can input the one or more first errors and the one or more second errors into the objective function of the in-situ style-transfer optimization algorithm, and the style-transfer component can accordingly execute the in-situ style-transfer optimization algorithm. Such execution can cause the style-transfer component to update or otherwise adjust the pixel values or voxel values of the previously-updated version of the medical image, so as minimize or otherwise reduce the objective function (e.g., so as to minimize or otherwise reduce the one or more first errors and the one or more second errors). Such updating or adjusting of the pixel values or voxel values of the previously-updated version of the medical image can yield a newly-updated version of the medical image. During a next or successive iteration, such newly-updated version of the medical image can be considered or otherwise treated as being the previously-updated version of the medical image.

In various instances, the style-transfer component can repeat such procedure any suitable number of times or otherwise until any suitable termination criterion is achieved. For example, the style-transfer component can repeat such procedure until the most recently calculated one or more first errors and the most recently calculated one or more second errors are both below any suitable thresholds. As another example, the style-transfer component can repeat such procedure until the sum of the most recently calculated one or more first errors and the most recently calculated one or more second errors is below any suitable threshold. In any case, there can be a final iteration, and whatever newly-updated version of the medical image that is produced during the final iteration or that has otherwise been most recently computed can be considered as the style-transferred medical image. By iteratively executing the in-situ style-transfer optimization algorithm based on activations extracted from the pre-trained neural network as described herein, the style-transfer component can accurately convert the first style or texture of the medical image into the second style or texture, without deteriorating the anatomical content of the medical image.

Note that, the style-transferred medical image can be generated in such fashion, notwithstanding the lack of a style-transfer neural network that has been trained on paired ground-truth annotations. Accordingly, the problems that plague existing techniques (e.g., misregistration, heightened radiation exposure) can be ameliorated.

Various embodiments described herein can be employed to use hardware or software to solve problems that are highly technical in nature (e.g., to facilitate task-specific image style transfer), that are not abstract and that cannot be performed as a set of mental acts by a human. Further, some of the processes performed can be performed by a specialized computer (e.g., deep learning neural networks having trainable internal parameters such as convolutional kernels) for carrying out defined acts related to task-specific image style transfer.

For example, such defined acts can include: accessing, by a device operatively coupled to a processor, a first medical image, wherein the first medical image can exhibit anatomical content and a first visual style; and generating, by the device and via execution of an optimization algorithm, a second medical image based on the first medical image, wherein the second medical image can exhibit the anatomical content and a second visual style that is different from the first visual style, and wherein the optimization algorithm can be based on (e.g., driven by) feature maps extracted from a pre-trained deep learning neural network that has been configured to perform an inferencing task on medical images exhibiting the second visual style. In particular, the device can iteratively execute the optimization algorithm on the first medical image, based on losses defined by the feature maps extracted from the pre-trained deep learning neural network, and the second medical image can be outputted by the optimization algorithm during a final iteration of such iterative execution.

In various instances, such defined acts can further comprise: accessing, by the device and during a current iteration of such iterative execution, an updated version of the first medical image that was produced by the optimization algorithm during a preceding iteration of such iterative execution; executing, by the device and during the current iteration, the pre-trained deep learning neural network on the updated version of the first medical image, wherein one or more shallow layers of the pre-trained deep learning neural network can produce one or more first feature maps based on the updated version of the first medical image, and wherein one or more deep layers of the pre-trained deep learning neural network can produce one or more second feature maps based on the updated version of the first medical image; executing, by the device, the pre-trained deep learning neural network on a representative medical image that exhibits the second visual style, wherein the one or more shallow layers of the pre-trained deep learning neural network can produce one or more third feature maps based on the representative medical image; executing, by the device, the pre-trained deep learning neural network on the first medical image, wherein the one or more deep layers of the pre-trained deep learning neural network can produce one or more fourth feature maps based on the first medical image; and updating, during the current iteration and via execution of the optimization algorithm, pixel values or voxel values of the updated version of the first medical image, based on first errors between the one or more first feature maps and the one or more third feature maps, and based on second errors between the one or more second feature maps and the one or more fourth feature maps, thereby yielding another updated version of the first medical image.

Such defined acts are not performed manually by humans. Indeed, neither the human mind nor a human with pen and paper can electronically access a medical image (e.g., a CT scanned image, an MRI scanned image, an X-ray scanned image) and electronically update pixel values or voxel values of the medical image by executing an optimization algorithm (e.g., stochastic gradient descent, Broyden-Fletcher-Goldfarb-Shanno) whose objective function is based on feature maps produced by hidden layers of a pre-trained neural network. Indeed, deep learning neural networks and in-situ optimization algorithms are inherently-computerized constructs that simply cannot be implemented in any way by the human mind without computers. Similarly, medical images are inherently computerized constructs that are generated or captured by electronic medical hardware (e.g., CT scanners, MRI scanners, X-ray scanners, PET scanners, ultrasound scanners) and not in any way by the human mind without computers. Accordingly, a computerized tool that can execute or otherwise implement a pre-trained deep learning neural network and an in-situ optimization algorithm to facilitate style-transfer of medical images is likewise inherently-computerized and cannot be implemented in any sensible, practical, or reasonable way without computers.

Moreover, various embodiments described herein can integrate into a practical application various teachings relating to task-specific image style transfer. As explained above, a deep learning neural network can be trained to perform an inferencing task (e.g., classification, segmentation, regression) on inputted medical images. However, the deep learning neural network cannot be expected to accurately perform the inferencing task on medical images that exhibit a style or texture that was not encountered by the deep learning neural network during training. To address this, various existing techniques first execute a style-transfer neural network on a given medical image so as to yield a style-transferred version of the given medical image, and such existing techniques then execute the deep learning neural network on the style-transferred version of the given medical image. Unfortunately, such existing techniques train the style-transfer neural network using large amounts of paired training data, and such large amounts of paired training data can be difficult to obtain in practice due to misregistration and radiation dosage concerns.

Various embodiments described herein can address one or more of these technical problems. Specifically, the present inventors devised various techniques for performing image style-transfer that do not involve curating large amounts of paired training data. In particular, rather than training a style-transfer neural network on paired ground-truth annotations, various embodiments described herein can iteratively execute an in-situ optimization algorithm whose objective function takes as arguments feature maps or activation maps produced by hidden layers of the deep learning neural network that has already been trained to perform the inferencing task. More specifically, some of such hidden layers can be considered as shallow layers, and others of such hidden layers can be considered as deep layers. In various instances, the shallow layers can be considered as being responsible for processing the style or texture of an inputted medical image, whereas the deep layers can be considered as being responsible for processing the anatomical content of the inputted medical image. So, various embodiments described herein can utilize the feature maps or activations produced by such shallow layers and by such deep layers to drive an in-situ style-transfer optimization algorithm (e.g., stochastic gradient descent algorithm, Broyden-Fletcher-Goldfarb-Shanno algorithm). In this way, style-transfer can be facilitated in the absence of paired ground-truth annotations, and thus without triggering misregistration and heightened radiation dosage concerns. Such embodiments certainly constitute concrete and tangible technical improvements in the field of image style transfer, and thus such embodiments clearly qualify as useful and practical applications of computers.

Furthermore, various embodiments described herein can control real-world tangible devices based on the disclosed teachings. For example, various embodiments described herein can electronically execute real-world deep learning neural networks on real-world medical images (e.g., CT images, MRI images, X-ray images, PET images, ultrasound images), and can electronically render any results produced by such real-world deep learning neural networks on real-world computer screens.

It should be appreciated that the herein figures and description provide non-limiting examples of various embodiments and are not necessarily drawn to scale.

FIG. 1 illustrates a block diagram of an example, non-limiting system 100 that can facilitate task-specific image style transfer in accordance with one or more embodiments described herein. As shown, a style-transfer system 102 can be electronically integrated, via any suitable wired or wireless electronic connections, with a medical image 104, with a pre-trained deep learning neural network 106, and with a representative medical image 118.

In various embodiments, the medical image 104 can visually depict or otherwise illustrate any suitable anatomical content. In other words, the medical image 104 can visually depict or otherwise illustrate any suitable number of any suitable anatomical structures of any suitable medical patient. As some non-limiting examples, such anatomical structures can include any suitable tissue of the medical patient (e.g., bone tissue, lung tissue, muscle tissue, brain tissue), any suitable organ of the medical patient (e.g., heart, liver, lung, brain, eye, colon, blood vessel), any suitable bodily fluid of the medical patient (e.g., blood, amniotic fluid), any other suitable body part of the medical patient, or any suitable portion thereof.

In various cases, the medical image 104 can have any suitable size, format, or dimensionality. As a non-limiting example, the medical image 104 can, in various aspects, be an x-by-y array of pixels, for any suitable positive integers x and y. As another non-limiting example, the medical image 104 can, in various instances, be an x-by-y-by-z array of voxels, for any suitable positive integers x, y, and z.

In various instances, the medical image 104 can be generated or otherwise captured by any suitable medical imaging device, medical imaging equipment, or medical imaging modality (not shown). As a non-limiting example, the medical image 104 can be generated or otherwise captured by a CT scanner, in which case the medical image 104 can be considered as a CT scanned image. As another non-limiting example, the medical image 104 can be generated or otherwise captured by an MRI scanner, in which case the medical image 104 can be considered as an MRI scanned image. As yet another non-limiting example, the medical image 104 can be generated or otherwise captured by a PET scanner, in which case the medical image 104 can be considered as a PET scanned image. As still another non-limiting example, the medical image 104 can be generated or otherwise captured by an X-ray scanner, in which case the medical image 104 can be considered as an X-ray scanned image. As even another non-limiting example, the medical image 104 can be generated or otherwise captured by an ultrasound scanner, in which case the medical image 104 can be considered as an ultrasound scanned image. Moreover, the medical image 104 can have undergone any suitable image reconstruction techniques, such as filtered back projection.

In various aspects, the medical image 104 can exhibit a first visual style/texture. In various instances, the first visual style/texture can be considered as being distinct from the anatomical content of the medical image 104. Indeed, in various cases, a brightness level with which the medical image 104 depicts or illustrates the anatomical content, a contrast level with which the medical image 104 depicts or illustrates the anatomical content, a blurriness level with which the medical image 104 depicts or illustrates the anatomical content, an optical noise level with which medical image 104 depicts or illustrates the anatomical content, a resolution level with which the medical image 104 depicts or illustrates the anatomical content, or any other suitable visually-perceptible characteristics or qualities with which the medical image 104 depicts or illustrates the anatomical content can collectively be considered as forming the first visual style/texture of the medical image 104. In various cases, the first visual style/texture of the medical image 104 can be considered as having been caused by whatever medical imaging device, medical imaging equipment, or medical imaging modality captured or generated the medical image 104.

Figure 2:
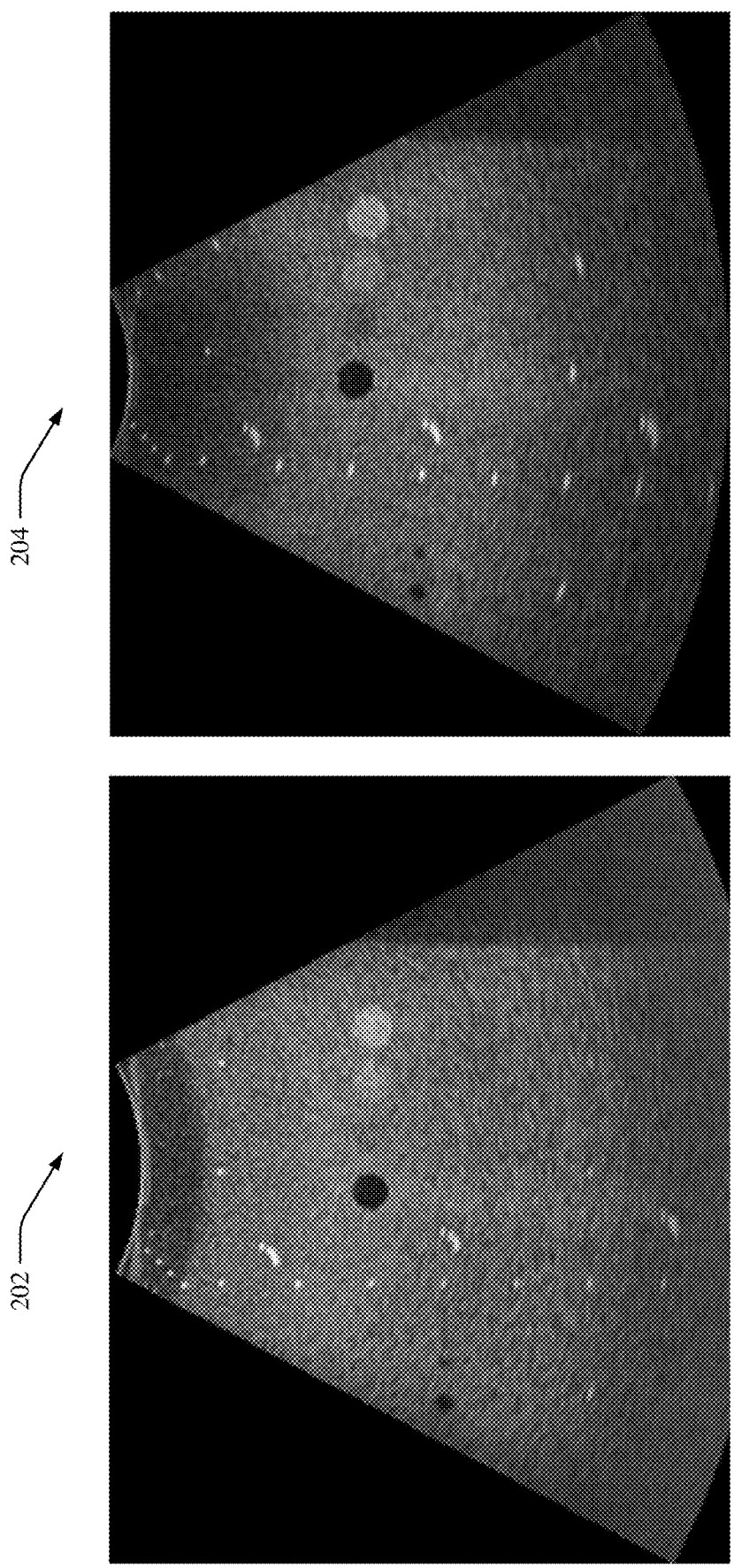
FIG. 2 illustrates example, non-limiting ultrasound scanned images having different visual styles or textures.

To help clarify the concept of visual style/texture, consider FIG. 2. FIG. 2 illustrates example, non-limiting ultrasound scanned images having different visual styles or textures. Indeed, as shown, FIG. 2 includes an ultrasound scanned image 202 and an ultrasound scanned image 204, both of which depict the same perspective view of the same laboratory sample as each other. Accordingly, the ultrasound scanned image 202 and the ultrasound scanned image 204 can be considered as illustrating the same anatomical content as each other. However, the ultrasound scanned image 202 was generated by a particular ultrasound scanner (e.g., Logiq scanner). In contrast, the ultrasound scanned image 204 was generated by a different ultrasound scanner (e.g., VScan Air Probe). As can be seen, although the ultrasound scanned image 202 and the ultrasound scanned image 204 depict the same anatomical content as each other, they exhibit different visual styles/textures. Indeed, the ultrasound scanned image 202 is brighter than the ultrasound scanned image 204, has a higher contrast level than the ultrasound scanned image 204, has less blurriness than the ultrasound scanned image 204, and has a higher resolution than the ultrasound scanned image 204. As FIG. 2 shows, visual style/texture can be considered as a type of visual information that is distinct from anatomical content. Moreover, as FIG. 2 also shows, two medical images can depict the same anatomical content as each other while simultaneously exhibiting different visual styles/textures.

Returning to FIG. 1, in various embodiments, the pre-trained deep learning neural network 106 can have or otherwise exhibit any suitable internal architecture. For instance, the pre-trained deep learning neural network 106 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable internal parameters can be convolutional kernels. As another example, any of such input layer, one or more hidden layers, or output layer can be dense layers, whose learnable or trainable internal parameters can be weight matrices or bias values. As still another example, any of such input layer, one or more hidden layers, or output layer can be batch normalization layers, whose learnable or trainable internal parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

In various aspects, the pre-trained deep learning neural network can be configured to perform any suitable inferencing task on an inputted medical. As a non-limiting example, the inferencing task can be image classification. In such case, the pre-trained deep learning neural network 106 can be configured to produce a classification label based on an inputted medical image. As another non-limiting example, the inferencing task can be image segmentation. In such case, the pre-trained deep learning neural network 106 can be configured to produce a pixel-wise or voxel-wise segmentation mask based on an inputted medical image. As another non-limiting example, the inferencing task can be image regression. In such case, the pre-trained deep learning neural network 106 can be configured to produce a regression result based on an inputted medical image (e.g., can produce one or more continuously variable scalars, continuously variable vectors, continuously variable matrices, or continuously variable tensors based on the inputted medical image).

In various instances, the pre-trained deep learning neural network 106 can have been trained (e.g., in supervised fashion, unsupervised fashion, or reinforcement learning fashion) on a second visual style/texture that is different from the first visual style/texture of the medical image 104. In other words, while undergoing training, the pre-trained deep learning neural network 106 can have encountered any suitable number of medical images, where each of such medical images can have exhibited the second visual style/texture instead of the first visual style/texture. In various aspects, this can occur when the medical images on which the pre-trained deep learning neural network 106 was trained were captured or generated by a different medical imaging modality than was used to capture or generate the medical image 104. In various other aspects, this can occur when the medical images on which the pre-trained deep learning neural network 106 was trained were captured or generated by the same medical imaging modality operating according to a different settings configuration than was used to capture or generate the medical image 104. In any case, because the pre-trained deep learning neural network 106 can have been trained on the second visual style/texture, the pre-trained deep learning neural network 106 can be expected to accurately perform the inferencing task only upon medical images that also exhibit the second visual style/texture.

In various cases, the representative medical image 118 can have the same format, size, or dimensionality as the medical image 104. For example, if the medical image 104 is an x-by-y pixel array that depicts one or more anatomical structures of a medical patient, then the representative medical image 118 can likewise be an x-by-y pixel array that depicts one or more respective anatomical structures of a respective medical patient. As another example, if the medical image 104 is an x-by-y-by-z voxel array that depicts one or more anatomical structures of a medical patient, then the representative medical image 118 can likewise be an x-by-y-by-z voxel array that depicts one or more respective anatomical structures of a respective medical patient.

In any case, the representative medical image 118 can exhibit the second visual style/texture, rather than the first visual style/texture. In various aspects, this can occur when the representative medical image 118 is captured or generated by the same medical imaging modality operating according to the same settings configuration as was used to capture or generate the medical images on which the pre-trained deep learning neural network 106 was trained. Indeed, in some instances, the representative medical image 118 can have been encountered by the pre-trained deep learning neural network 106 during training. In various cases, because the representative medical image 118 can exhibit the second visual style/texture, and because the pre-trained deep learning neural network 106 can have been trained on the second visual style/texture, the representative medical image 118 can be considered as representing the visual style/texture on which the pre-trained deep learning neural network 106 was trained, hence the term "representative."

Note that the representative medical image 118 can depict any suitable anatomical content, and that such anatomical content can be different from the anatomical content depicted by the medical image 104. In other words, the medical image 104 and the representative medical image 118 can depict different anatomical content (e.g., different anatomical structures of different medical patients) than each other.

In various aspects, it can be desired for the inferencing task to be performed with respect to the anatomical content depicted or illustrated by the medical image 104. However, because the pre-trained deep learning neural network 106 was trained on the second visual style/texture, and because the medical image 104 exhibits the first visual style/texture rather than the second visual style/texture, the pre-trained deep learning neural network 106 cannot be expected to accurately perform the inferencing task directly on the medical image 104.

As described herein, the style-transfer system 102 can address this problem, by leveraging the representative medical image 118.

In various embodiments, the style-transfer system 102 can comprise a processor 108 (e.g., computer processing unit, microprocessor) and a non-transitory computer-readable memory 110 that is operably or operatively or communicatively connected or coupled to the processor 108. The non-transitory computer-readable memory 110 can store computer-executable instructions which, upon execution by the processor 108, can cause the processor 108 or other components of the style-transfer system 102 (e.g., access component 112, style-transfer component 114, execution component 116) to perform one or more acts. In various embodiments, the non-transitory computer-readable memory 110 can store computer-executable components (e.g., access component 112, style-transfer component 114, execution component 116), and the processor 108 can execute the computer-executable components.

In various embodiments, the style-transfer system 102 can comprise an access component 112. In various aspects, the access component 112 can electronically receive or otherwise electronically access the medical image 104, the pre-trained deep learning neural network 106, or the representative medical image 118. In various instances, the access component 112 can electronically retrieve the medical image 104, the pre-trained deep learning neural network 106, or the representative medical image 118 from any suitable centralized or decentralized data structures (not shown) or from any suitable centralized or decentralized computing devices (not shown). As a non-limiting example, whatever medical imaging device, equipment, or modality (e.g., CT scanner, MRI scanner, X-ray scanner, PET scanner, ultrasound scanner) that generated or captured the medical image 104 can transmit the medical image 104, the pre-trained deep learning neural network 106, or the representative medical image 118 to the access component 112. In any case, the access component 112 can electronically obtain or access the medical image 104, the pre-trained deep learning neural network 106, or the representative medical image 118, such that other components of the style-transfer system 102 can electronically interact with the medical image 104, with the pre-trained deep learning neural network 106, or with the representative medical image 118.

In various embodiments, the style-transfer system 102 can comprise a style-transfer component 114. In various aspects, as described herein, the style-transfer component 114 can iteratively execute an in-situ style-transfer optimization algorithm based on the medical image 104, based on the pre-trained deep learning neural network 106, and based on the representative medical image 118, thereby yielding a style-transferred medical image.

In various embodiments, the style-transfer system 102 can comprise an execution component 116. In various instances, as described herein, the execution component 116 can execute the pre-trained deep learning neural network 106 on the style-transferred medical image, thereby yielding an inferencing task result.

Figure 3:
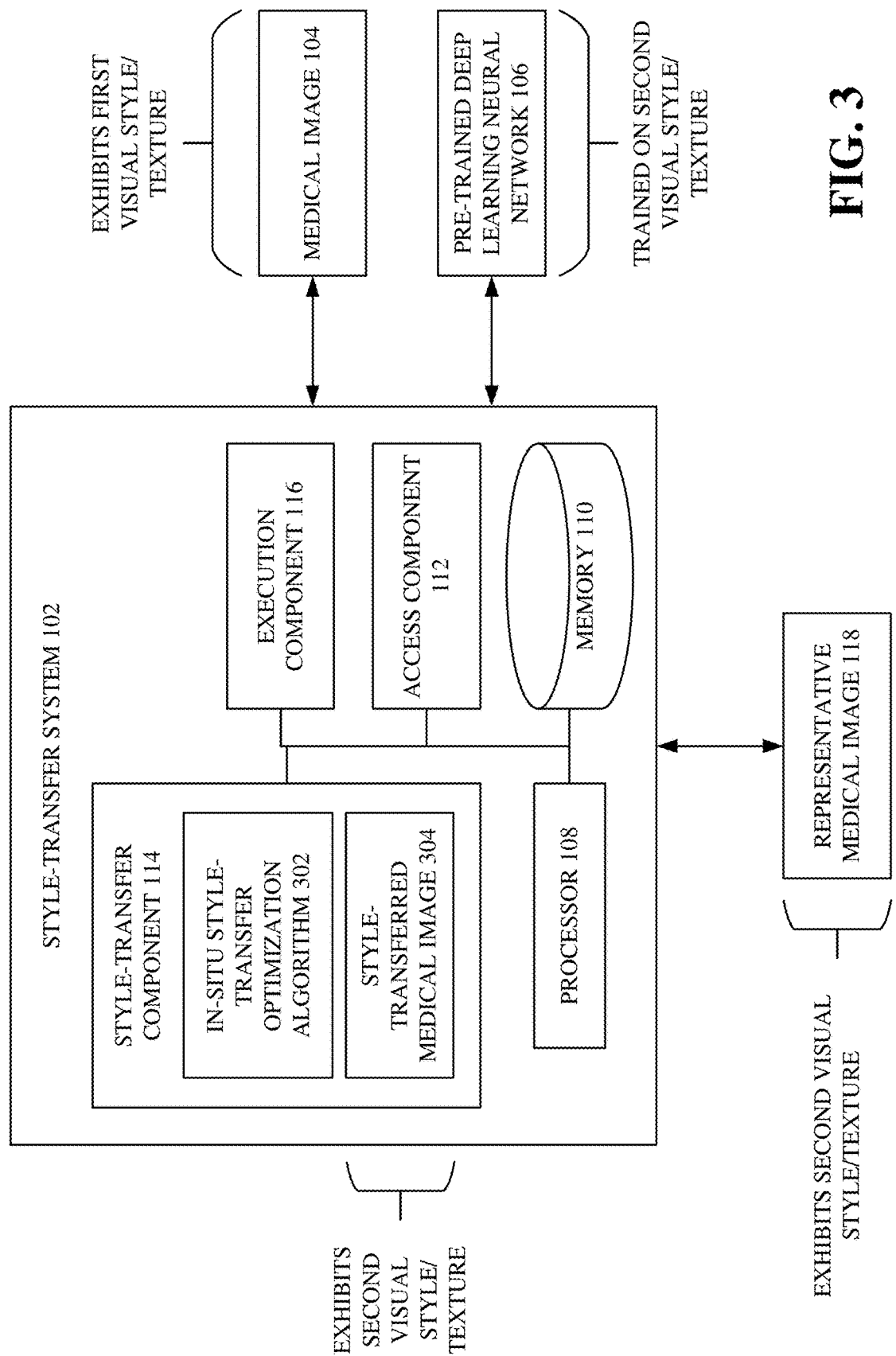
FIG. 3 illustrates a block diagram of an example, non-limiting system including an in-situ style-transfer optimization algorithm and a style-transferred medical image that facilitates task-specific image style transfer in accordance with one or more embodiments described herein.

FIG. 3 illustrates a block diagram of an example, non-limiting system 300 including an in-situ style-transfer optimization algorithm and a style-transferred medical image that can facilitate task-specific image style transfer in accordance with one or more embodiments described herein. As shown, the system 300 can, in some cases, comprise the same components as the system 100, and can further comprise an in-situ style-transfer optimization algorithm 302 and a style-transferred medical image 304.

In various embodiments, the style-transfer component 114 can electronically store, electronically maintain, electronically control, or otherwise electronically access the in-situ style-transfer optimization algorithm 302. In various aspects, the in-situ style-transfer optimization algorithm 302 can be any suitable sequence or series of mathematical operations which, when performed, can optimize (e.g., can identify or approximate a local or global minimum) of an objective function. In various instances, the objective function can be any suitable mathematical function or combination of mathematical functions. As a non-limiting example, the objective function can include any suitable number of any suitable types of linear functions or any suitable number of any suitable types of non-linear functions, any of which can be combined together additively, multiplicatively, exponentially, or even in nested fashion. In various cases, the objective function can be considered as depending upon any suitable number of independent variables. In other words, the magnitude of the objective function can vary with the values of such independent variables. Accordingly, in various aspects, performance or execution of the in-situ style-transfer optimization algorithm 302 can reveal how the values of those independent variables should be incrementally adjusted so as to correspondingly incrementally reduce the magnitude of the objective function. As a non-limiting example, the in-situ style-transfer optimization algorithm 302 can determine how to adjust the values of the independent variables via a stochastic gradient descent technique. As another non-limiting example, the in-situ style-transfer optimization algorithm 302 can determine how to adjust the values of the independent variables via a Broyden-Fletcher-Goldfarb-Shanno technique. In any case, performance or execution of the in-situ style-transfer optimization algorithm 302 can involve or otherwise include actually adjusting the values of the independent variables in such fashion, thereby causing the magnitude of the objective function to become actually reduced. Thus, iterative performance or iterative execution of the in-situ style-transfer optimization algorithm 302 can be considered as repeatedly adjusting the values of the independent variables so as to cause the magnitude of the objective function to become minimized or approximately minimized.

In various instances, the pixel values or voxel values of the medical image 104 can be considered or otherwise treated as the independent variables of the in-situ style-transfer optimization algorithm 302. Moreover, in various cases, the objective function of the in-situ style-transfer optimization algorithm 302 can take as arguments feature maps (e.g., activations) generated by hidden layers of the pre-trained deep learning neural network 106, which feature maps the hidden layers can produce in response to the pre-trained deep learning neural network 106 being executed on the medical image 104 and on the representative medical image 118. Therefore, in various aspects, the style-transfer component 114 can iteratively execute or otherwise perform the in-situ style-transfer optimization algorithm 302 on the medical image 104, where such iterative execution can cause the style-transfer component 114 to update or otherwise adjust the pixel values or voxel values of the medical image 104 at each iteration, where such iterative adjustments can cause the objective function to become minimized or approximately minimized. After completion of all iterations (e.g., when any suitable optimization termination criterion is achieved), the end-result can be the style-transferred medical image 304.

In various aspects, the style-transferred medical image 304 can have the same size, format, or dimensionality as the medical image 104. As a non-limiting example, if the medical image 104 is an x-by-y array of pixels, then the style-transferred medical image 304 can likewise be an x-by-y array of pixels. As another non-limiting example, if the medical image 104 is an x-by-y-by-z array of voxels, then the style-transferred medical image 304 can likewise be an x-by-y-by-z array of voxels. In various instances, the style-transferred medical image 304 can depict or otherwise illustrate the same anatomical content as the medical image 104. In other words, the style-transferred medical image 304 can visually show the same perspective view of the same anatomical structures of the same medical patient as is shown in the medical image 104. However, in various cases, the style-transferred medical image 304 can exhibit the second visual style/texture, instead of the first visual style/texture. That is, the in-situ style-transfer optimization algorithm 302 can be considered as altering the pixel values or voxel values of the medical image 104, so as to change, shift, or otherwise transform the visual style/texture of the medical image 104 from the first visual style/texture to the second visual style/texture, while also preserving (e.g., not altering) the anatomical content of the medical image 104.

Figure 4:
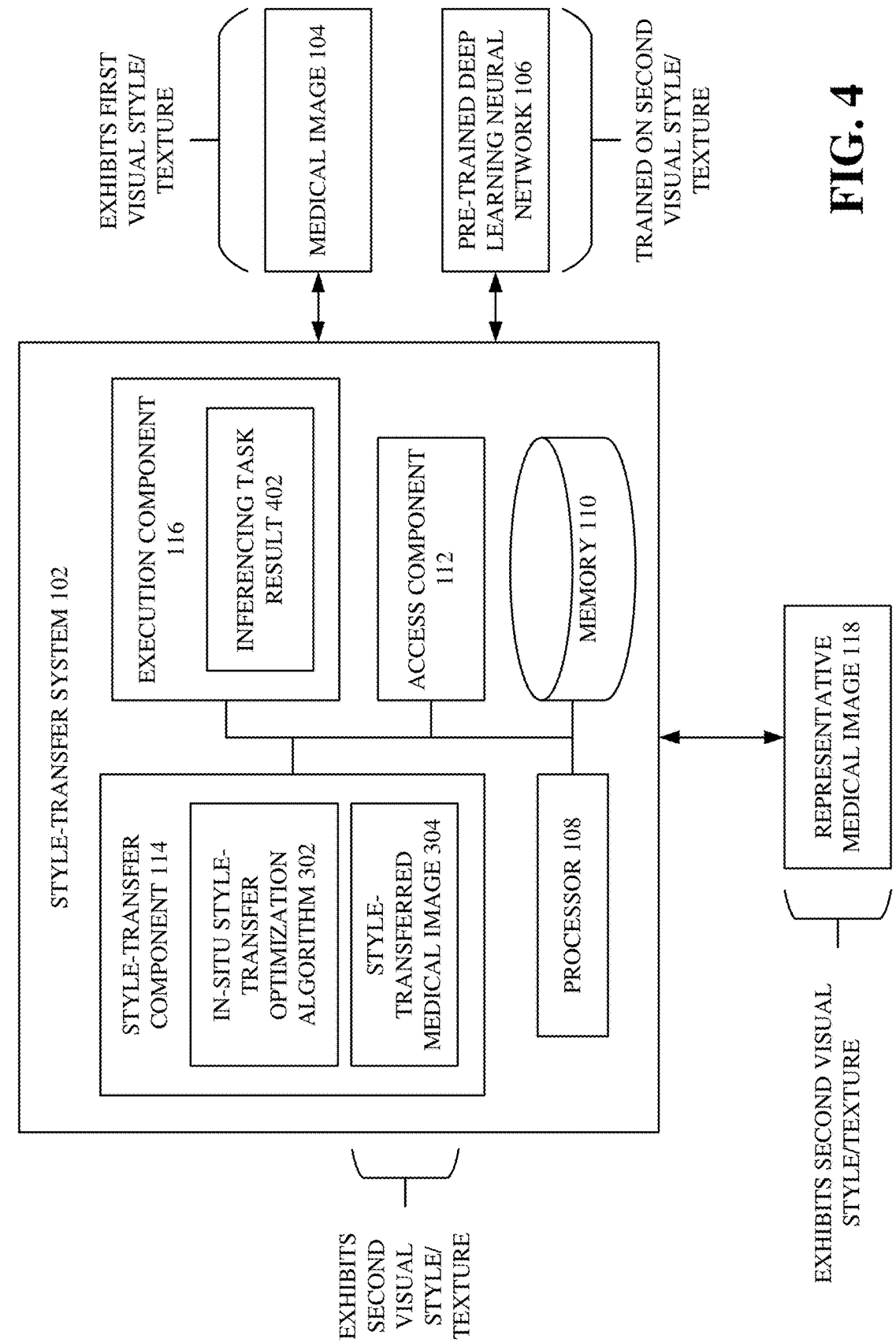
FIG. 4 illustrates a block diagram of an example, non-limiting system including an inferencing task result that facilitates task-specific image style transfer in accordance with one or more embodiments described herein.

FIG. 4 illustrates a block diagram of an example, non-limiting system 400 including an inferencing task result that can facilitate task-specific image style transfer in accordance with one or more embodiments described herein. As shown, the system 400 can, in some cases, comprise the same components as the system 300, and can further comprise an inferencing task result 402.

In various aspects, the execution component 116 can electronically execute the pre-trained deep learning neural network 106 on the style-transferred medical image 304, and such execution can cause the pre-trained deep learning neural network 106 to produce the inferencing task result 402. Various non-limiting aspects are further described with respect to FIG. 5.

Figure 5:
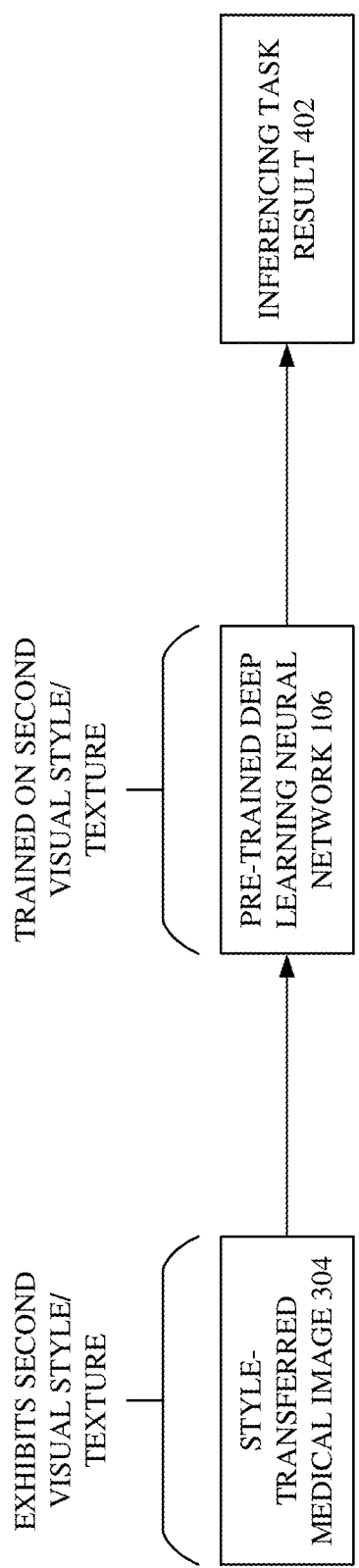
FIG. 5 illustrates an example, non-limiting block diagram showing how an inferencing task result can be generated in accordance with one or more embodiments described herein.

FIG. 5 illustrates an example, non-limiting block diagram 500 showing how the inferencing task result 402 can be generated in accordance with one or more embodiments described herein.

In various aspects, the execution component 116 can electronically execute the pre-trained deep learning neural network 106 on the style-transferred medical image 304, thereby causing the pre-trained deep learning neural network 106 to produce the inferencing task result 402. More specifically, the execution component 116 can provide or otherwise pass the style-transferred medical image 304 to an input layer of the pre-trained deep learning neural network 106. In various instances, the style-transferred medical image 304 can complete a forward pass through one or more hidden layers of the pre-trained deep learning neural network 106. In various cases, an output layer of the pre-trained deep learning neural network 106 can compute or otherwise calculate the inferencing task result 402, based on activations generated by the one or more hidden layers of the pre-trained deep learning neural network 106.

In various aspects, the inferencing task result 402 can be any suitable electronic data having any suitable size, format, or dimensionality. As a non-limiting example, the inferencing task result 402 can be one or more scalars, one or more vectors, one or more matrices, one or more tensors, one or more character strings, or any suitable combination thereof. In various instances, the size, format, or dimensionality of the inferencing task result 402 can depend upon the inferencing task that the pre-trained deep learning neural network 106 is configured to perform. As a non-limiting example, suppose that the inferencing task is image classification. In such case, the inferencing task result 402 can be a dichotomous or multi-chotomous classification label that the pre-trained deep learning neural network 106 has generated for or otherwise based on the style-transferred medical image 304. As another non-limiting example, suppose that the inferencing task is image segmentation. In such case, the inferencing task result 402 can be a pixel-wise or voxel-wise segmentation mask that the pre-trained deep learning neural network 106 has generated for or otherwise based on the style-transferred medical image 304. As yet another non-limiting example, suppose that the inferencing task is image regression. In such case, the inferencing task result 402 can be a continuously-variable regression result that the pre-trained deep learning neural network 106 has generated for or otherwise based on the style-transferred medical image 304. In some non-limiting instances, such continuously-variable regression result can be a denoised version of the style-transferred medical image 304, can be a resolution-enhanced version of the style-transferred medical image 304, or can be a latent vector representing in compressed fashion the style-transferred medical image 304.

In any case, because the pre-trained deep learning neural network 106 can have been trained on (e.g., can have been trained to handle) the second visual style/texture, and because the style-transferred medical image 304 can exhibit the second visual style/texture, the pre-trained deep learning neural network 106 can be expected to accurately or otherwise reliably perform the inferencing task on the style-transferred medical image 304. In other words, the inferencing task result 402 can be associated with a high degree of confidence, due to the style/texture match between the style-transferred medical image 304 and the pre-trained deep learning neural network 106. In contrast, because the pre-trained deep learning neural network 106 can have been trained on (e.g., can have been trained to handle) the second visual style/texture, and because the medical image 104 can exhibit the first visual style/texture, the pre-trained deep learning neural network 106 cannot be expected to accurately or otherwise reliably perform the inferencing task on the medical image 104. In other words, if an inferencing task result were produced by executing the pre-trained deep learning neural network 106 directly on the medical image 104 (e.g., without first shifting its visual style/texture via the in-situ style-transfer optimization algorithm 302), such inferencing task result would be associated with a low degree of confidence, due to the style-texture mismatch between the medical image 104 and the pre-trained deep learning neural network 106. However, because the style-transferred medical image 304 can have the same anatomical content as the medical image 104, the inferencing task result 402 can be considered as the result that would be obtained if the inferencing task were accurately or reliably performed on the medical image 104. Thus, the style-transfer system 102 can be considered as having enlarged the generalizability or applicability of the pre-trained deep learning neural network 106. In other words, the style-transfer system 102 can allow the pre-trained deep learning neural network 106 to be executed on anatomical content depicted by medical images which the pre-trained deep learning neural network 106 could not have reliably processed otherwise.

In various aspects, the execution component 116 can electronically render the inferencing task result 402 or the style-transferred medical image 304 on any suitable electronic display (not shown). In various other aspects, the execution component 116 can electronically transmit or share the inferencing task result 402 or the style-transferred medical image 304 with any other suitable computing devices (not shown).

Various more specific details regarding how the in-situ style-transfer optimization algorithm 302 can be iteratively executed so as to generate the style-transferred medical image 304 are described with respect to FIGS. 6-9. In particular, FIGS. 6-9 illustrate example, non-limiting block diagrams 600, 700, 800, and 900 showing how the in-situ style-transfer optimization algorithm 302 can be implemented based on the pre-trained deep learning neural network 106 in accordance with one or more embodiments described herein.

Note that, throughout iterative execution of the in-situ style-transfer optimization algorithm 302, any trainable internal parameters (e.g., convolutional kernels, weight matrices, bias values) of the pre-trained deep learning neural network 106 can be frozen, preserved, or otherwise unaltered.

Figure 6:
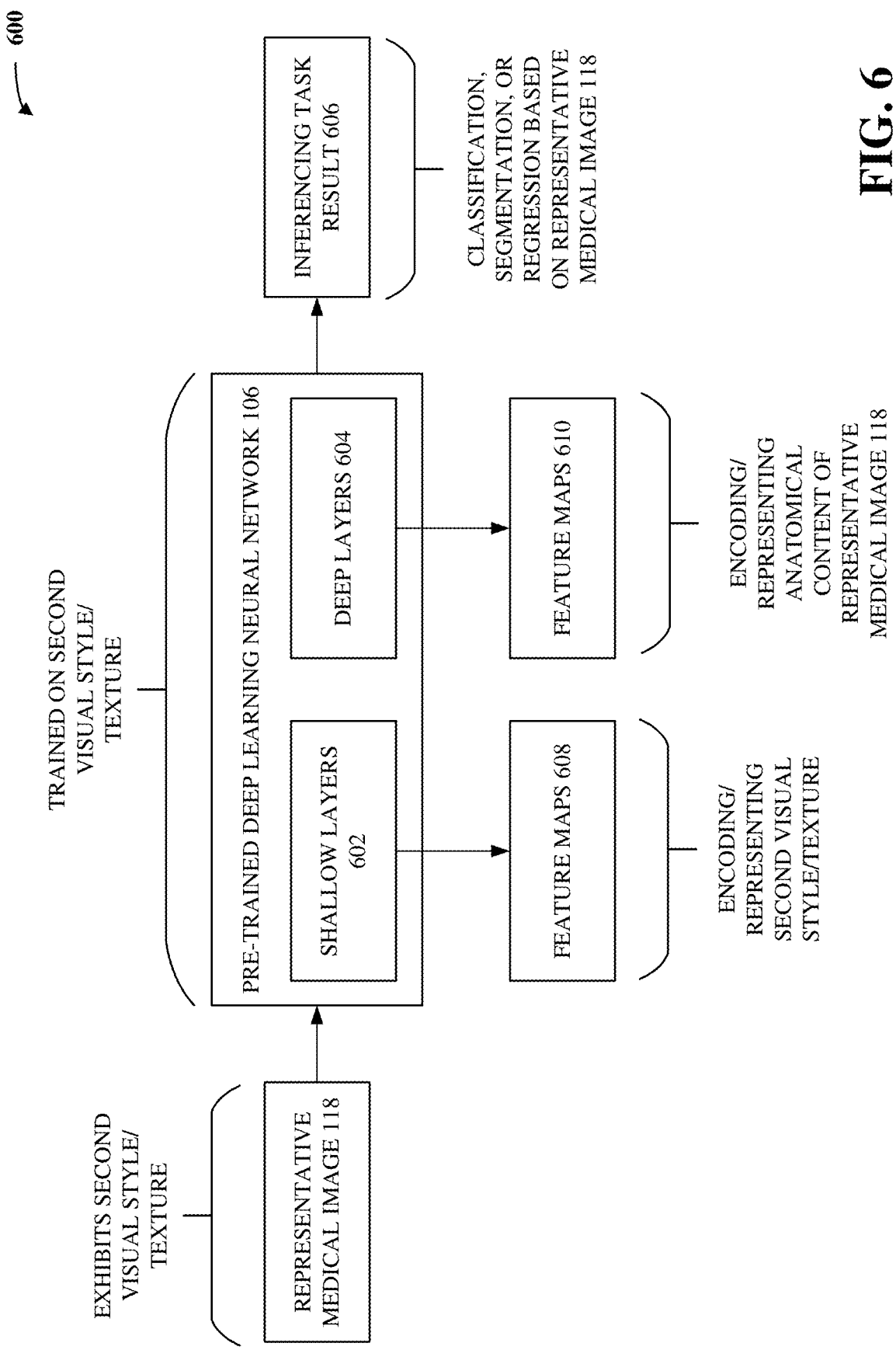
FIGS. 6-9 illustrate example, non-limiting block diagrams showing how an in-situ style-transfer optimization algorithm can be implemented based on a pre-trained deep learning neural network in accordance with one or more embodiments described herein.

Now, consider FIG. 6. In various aspects, as shown, the style-transfer component 114 can electronically execute the pre-trained deep learning neural network 106 on the representative medical image 118. That is, the style-transfer component 114 can feed, supply, or otherwise input the representative medical image 118 to the pre-trained deep learning neural network 106, and the representative medical image 118 can thus complete a forward pass through whatever neural network layers make up the pre-trained deep learning neural network 106.

As shown in FIG. 6, the pre-trained deep learning neural network 106 can, in various aspects, comprise a set of shallow layers 602 and a set of deep layers 604. In various instances, the set of shallow layers 602 can include any suitable number of layers within the pre-trained deep learning neural network 106. As a non-limiting example, the set of shallow layers 602 can comprise a total of $n_{shallow}$ layers, for any suitable positive integer $n_{shallow}$. Similarly, the set of deep layers 604 can include any suitable number of layers within the pre-trained deep learning neural network 106. As a non-limiting example, the set of deep layers 604 can comprise a total of $n_{deep}$ layers, for any suitable positive integer $n_{deep}$. In various aspects, the set of shallow layers 602 and the set of deep layers 604 can be disjoint with each other and can be considered as collectively forming a subset of whatever hidden layers make up the pre-trained deep learning neural network 106. In other words, the pre-trained deep learning neural network 106 can comprise an input layer, an output layer, and any suitable number of hidden layers between the input layer and the output layer, where the cardinality (e.g., total number) of such hidden layers can be greater than or equal to $n_{shallow}+n_{deep}$.

In any case, the set of shallow layers 602 can be considered as a strict subset of the hidden layers of the pre-trained deep learning neural network 106 that are positioned near (e.g., within any suitable threshold distance of) the input layer of the pre-trained deep learning neural network 106. In contrast, the set of deep layers 604 can be considered as a strict subset of the hidden layers of the pre-trained deep learning neural network 106 that are positioned downstream of the set of shallow layers 602.

In various aspects, because the set of shallow layers 602 can be positioned more upstream in the pre-trained deep learning neural network 106, the set of shallow layers 602 can be considered as being a portion of the pre-trained deep learning neural network 106 that is responsible for performing a more superficial or surface-level analysis on inputted medical images. In other words, when the pre-trained deep learning neural network 106 is executed on an inputted medical image, the set of shallow layers 602 can be considered as being responsible for processing or otherwise analyzing at least some aspects of whatever visual style/texture is exhibited by that inputted medical image. In still other words, the set of shallow layers 602 can be considered as identifying or capturing at least some details of the visual style/texture of that inputted medical image that are relevant with respect to the inferencing task (e.g., classification, segmentation, regression) that the pre-trained deep learning neural network 106 is configured to perform.

In contrast, because the set of deep layers 604 can be positioned more downstream in the pre-trained deep learning neural network 106, the set of deep layers 604 can be considered as being a portion of the pre-trained deep learning neural network 106 that is responsible for performing a less superficial or surface-level analysis on inputted medical images. In other words, when the pre-trained deep learning neural network 106 is executed on an inputted medical image, the set of deep layers 604 can be considered as being responsible for processing or otherwise analyzing at least some aspects of whatever anatomical content is exhibited by that inputted medical image. In still other words, the set of deep layers 604 can be considered as identifying or capturing at least some details of the anatomical content of that inputted medical image that are relevant with respect to the inferencing task (e.g., classification, segmentation, regression) that the pre-trained deep learning neural network 106 is configured to perform.

Now, as mentioned above, the style-transfer component 114 can electronically execute the pre-trained deep learning neural network 106 on the representative medical image 118. In various aspects, this can cause the pre-trained deep learning neural network 106 to generate as output an inferencing task result 606. In particular, the style-transfer component 114 can feed the representative medical image 118 to the input layer of the pre-trained deep learning neural network 106, the representative medical image 118 can complete a forward pass through the hidden layers of the pre-trained deep learning neural network 106, and the output layer of the pre-trained deep learning neural network 106 can compute the inferencing task result 606 based on feature maps (e.g., activations) produced by the hidden layers of the pre-trained deep learning neural network 106.

In various instances, the inferencing task result 606 can have the same size, format, or dimensionality as the inferencing task result 402. As a non-limiting example, if the inferencing task is image classification, then the inferencing task result 606 can be a classification label that the pre-trained deep learning neural network 106 has generated for the representative medical image 118. As another non-limiting example, if the inferencing task is image segmentation, then the inferencing task result 606 can be a pixel-wise or voxel-wise segmentation mask that the pre-trained deep learning neural network 106 has generated for the representative medical image 118. As still another non-limiting example, if the inferencing task is image regression, then the inferencing task result 606 can be a regression result (e.g., denoised version, resolution-enhanced version, latent vector representation) that the pre-trained deep learning neural network 106 has generated for the representative medical image 118. In any case, because the representative medical image 118 can exhibit the second visual style/texture, and because the pre-trained deep learning neural network 106 can have been trained to handle the second visual style/texture, the inferencing task result 606 can be considered as accurate, correct, or otherwise reliable.

Because the pre-trained deep learning neural network 106 can comprise the set of shallow layers 602 and the set of deep layers 604, execution of the pre-trained deep learning neural network 106 on the representative medical image 118 can cause the representative medical image 118 to pass through the set of shallow layers 602 and through the set of deep layers 604.

In various aspects, as the representative medical image 118 passes through the set of shallow layers 602, the set of shallow layers 602 can produce a set of feature maps 608. In various instances, each of the set of shallow layers 602 can generate one or more of the set of feature maps 608. Accordingly, the set of feature maps 608 can comprise a total of $f_{shallow}$ feature maps, for any suitable positive integer $f_{shallow} \geq N_{shallow}$. In various cases, a feature map in the set of feature maps 608 can be any suitable electronic data having any suitable size, format, or dimensionality. As a non-limiting example, any of the set of feature maps 608 can be a scalar. As another non-limiting example, any of the set of feature maps 608 can be a vector. As still another non-limiting example, any of the set of feature maps 608 can be a matrix. As even another non-limiting example, any of the set of feature maps 608 can be a tensor. As yet another non-limiting example, any of the set of feature maps 608 can be any suitable combination of scalars, vectors, matrices, or tensors. In various aspects, because the set of shallow layers 602 can be considered as being responsible for processing the visual style/texture of an inputted medical image, the set of feature maps 608 can be considered as representing, encoding, or otherwise being relevant to the visual style/texture that is exhibited by the representative medical image 118. That is, the set of feature maps 608 can be considered as representing, encoding or otherwise being relevant to the second visual style/texture.

Similarly, as the representative medical image 118 passes through the set of deep layers 604, the set of deep layers 604 can produce a set of feature maps 610. In various instances, each of the set of deep layers 604 can generate one or more of the set of feature maps 610. So, the set of feature maps 610 can comprise a total of $f_{deep}$ feature maps, for any suitable positive integer $f_{deep} \geq n_{deep}$. In various cases, and just as above, a feature map in the set of feature maps 610 can be any suitable electronic data having any suitable size, format, or dimensionality. As a non-limiting example, any of the set of feature maps 610 can be a scalar. As another non-limiting example, any of the set of feature maps 610 can be a vector. As still another non-limiting example, any of the set of feature maps 610 can be a matrix. As even another non-limiting example, any of the set of feature maps 610 can be a tensor. As yet another non-limiting example, any of the set of feature maps 610 can be any suitable combination of scalars, vectors, matrices, or tensors. In various aspects, since the set of deep layers 604 can be considered as being responsible for processing the anatomical content of an inputted medical image, the set of feature maps 610 can be considered as representing, encoding, or otherwise being relevant to whatever anatomical content that is exhibited by the representative medical image 118.

In various instances, the inferencing task result 606 and the set of feature maps 610 can be considered as irrelevant for performing the in-situ style-transfer optimization algorithm 302. In contrast, the set of feature maps 608 can, as described herein, be considered as relevant for performing the in-situ style-transfer optimization algorithm 302. Accordingly, the style-transfer component 114 can, in some cases, discard the inferencing task result 606 and the set of feature maps 610, and the style-transfer component 114 can store, record, or otherwise preserve the set of feature maps 608.

Figure 7:
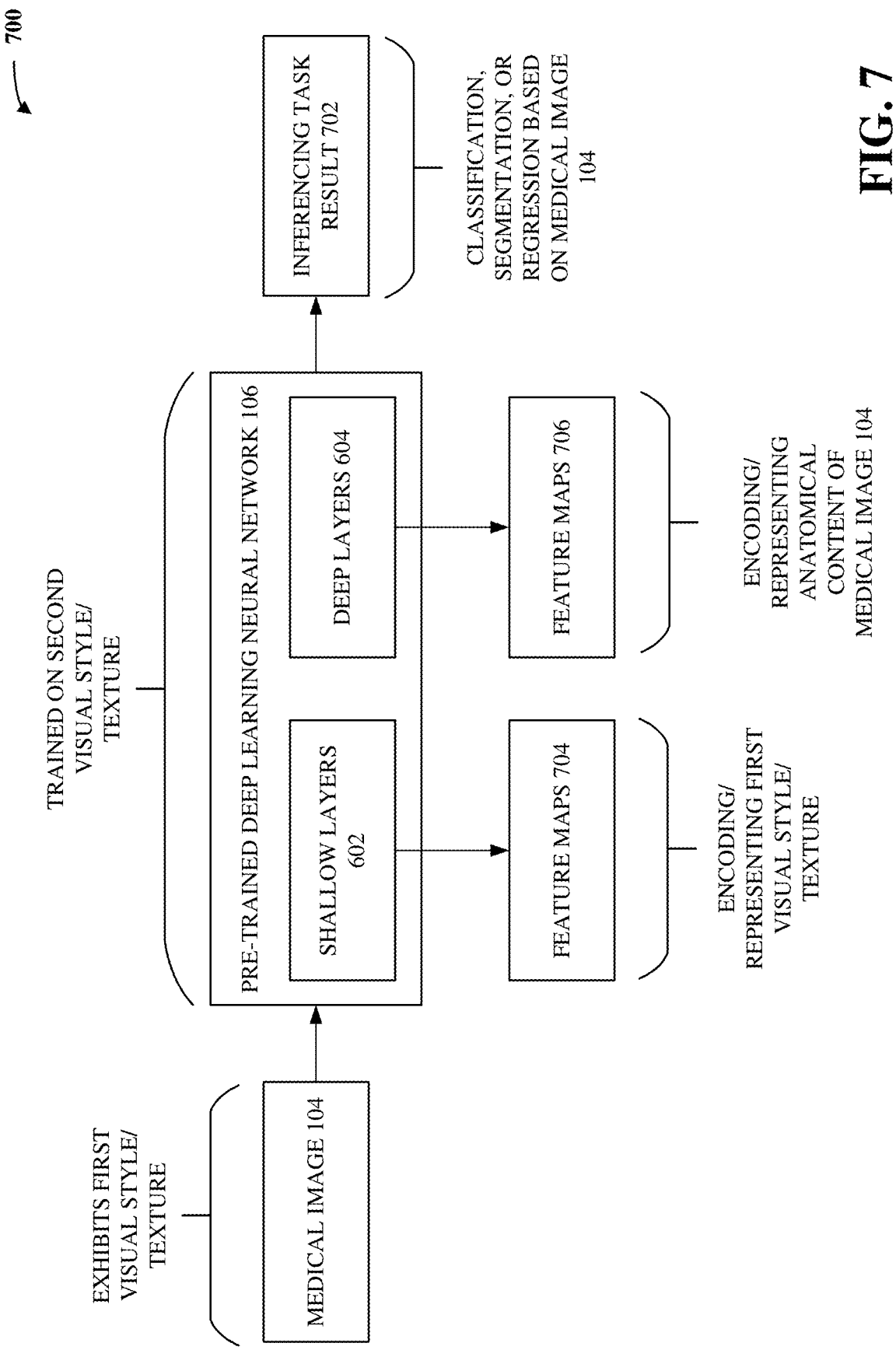

Next, consider FIG. 7. In various aspects, the style-transfer component 114 can electronically execute the pre-trained deep learning neural network 106 on the medical image 104. In various aspects, this can cause the pre-trained deep learning neural network 106 to generate as output an inferencing task result 702. In particular, the style-transfer component 114 can feed the medical image 104 to the input layer of the pre-trained deep learning neural network 106, the medical image 104 can complete a forward pass through the hidden layers of the pre-trained deep learning neural network 106, and the output layer of the pre-trained deep learning neural network 106 can compute the inferencing task result 702 based on feature maps (e.g., activations) produced by the hidden layers of the pre-trained deep learning neural network 106.

In various instances, the inferencing task result 702 can have the same size, format, or dimensionality as the inferencing task result 402. As a non-limiting example, if the inferencing task is image classification, then the inferencing task result 702 can be a classification label that the pre-trained deep learning neural network 106 has generated for the medical image 104. As another non-limiting example, if the inferencing task is image segmentation, then the inferencing task result 702 can be a pixel-wise or voxel-wise segmentation mask that the pre-trained deep learning neural network 106 has generated for the medical image 104. As still another non-limiting example, if the inferencing task is image regression, then the inferencing task result 702 can be a regression result (e.g., denoised version, resolution-enhanced version, latent vector representation) that the pre-trained deep learning neural network 106 has generated for the medical image 104. In any case, because the medical image 104 can exhibit the first visual style/texture, and because the pre-trained deep learning neural network 106 can have been trained to handle the second visual style/texture, the inferencing task result 702 can be considered as inaccurate, incorrect, or otherwise unreliable.

Because the pre-trained deep learning neural network 106 can comprise the set of shallow layers 602 and the set of deep layers 604, execution of the pre-trained deep learning neural network 106 on the medical image 104 can cause the medical image 104 to pass through the set of shallow layers 602 and through the set of deep layers 604.

In various aspects, as the medical image 104 passes through the set of shallow layers 602, the set of shallow layers 602 can produce a set of feature maps 704. Just like the set of feature maps 608, the set of feature maps 704 can comprise a total of $f_{shallow}$ feature maps, where each of the set of feature maps 704 can have the same size, format, or dimensionality as a respective one of the set of feature maps 608. In various aspects, because the set of shallow layers 602 can be considered as being responsible for processing the visual style/texture of an inputted medical image, the set of feature maps 704 can be considered as representing, encoding, or otherwise being relevant to the visual style/texture that is exhibited by the medical image 104. That is, the set of feature maps 704 can be considered as representing, encoding or otherwise being relevant to the first visual style/texture.

Similarly, as the medical image 104 passes through the set of deep layers 604, the set of deep layers 604 can produce a set of feature maps 706. Just like the set of feature maps 610, the set of feature maps 706 can comprise a total of $f_{deep}$ feature maps, where each of the set of feature maps 706 can have the same size, format, or dimensionality as a respective one of the set of feature maps 610. In various instances, because the set of deep layers 604 can be considered as being responsible for processing the anatomical content of an inputted medical image, the set of feature maps 706 can be considered as representing, encoding, or otherwise being relevant to whatever anatomical content that is exhibited by the medical image 104.

In various cases, the inferencing task result 702 and the set of feature maps 704 can be considered as irrelevant for performing the in-situ style-transfer optimization algorithm 302. In contrast, the set of feature maps 706 can, as described herein, be considered as relevant for performing the in-situ style-transfer optimization algorithm 302. Accordingly, the style-transfer component 114 can, in some cases, discard the inferencing task result 702 and the set of feature maps 704, and the style-transfer component 114 can store, record, or otherwise preserve the set of feature maps 706.

Figure 8:
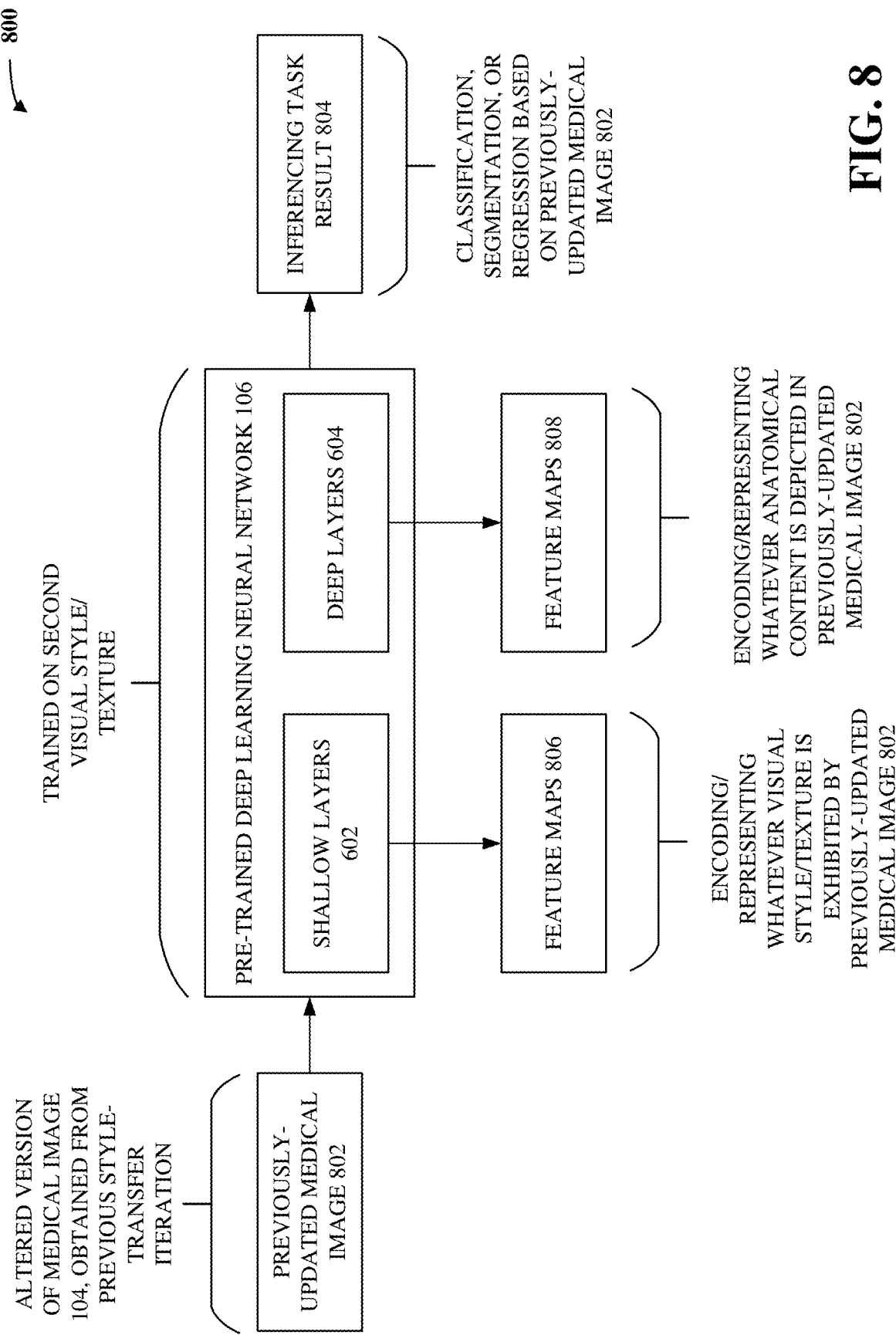

Next, consider FIG. 8. In various aspects, the style-transfer component 114 can electronically access a previously-updated medical image 802. In various instances, the previously-updated medical image 802 can be considered as being whatever altered, adjusted, or modified version of the medical image 104 was produced during or otherwise as a result of an immediately preceding execution or performance of the in-situ style-transfer optimization algorithm 302. Accordingly, in various cases, the previously-updated medical image 802 can have the same format, size, or dimensionality as the medical image 104 (e.g., can be an x-by-y pixel array if the medical image 104 is an x-by-y pixel array; can be an x-by-y-by-z voxel array if the medical image 104 is an x-by-y-by-z voxel array). However, the previously-updated medical image 802 can, in various aspects, have different pixel values or different voxel values than the medical image 104, due to such pixel values or voxel values having been adjusted or otherwise changed by the immediately previous iteration of the in-situ style-transfer optimization algorithm 302. Note that, in various aspects, the very first iteration of the in-situ style-transfer optimization algorithm 302 can be considered as having no immediately preceding iteration. In such case, the medical image 104 itself (e.g., the original version of the medical image 104) can be considered or otherwise treated as the previously-updated medical image 802.

In various instances, the style-transfer component 114 can electronically execute the pre-trained deep learning neural network 106 on the previously-updated medical image 802. In various aspects, this can cause the pre-trained deep learning neural network 106 to generate as output an inferencing task result 804. In particular, the style-transfer component 114 can feed the previously-updated medical image

802 to the input layer of the pre-trained deep learning neural network 106, the previously-updated medical image 802 can complete a forward pass through the hidden layers of the pre-trained deep learning neural network 106, and the output layer of the pre-trained deep learning neural network 106 can compute the inferencing task result 804 based on feature maps (e.g., activations) produced by the hidden layers of the pre-trained deep learning neural network 106.

In various instances, the inferencing task result 804 can have the same size, format, or dimensionality as the inferencing task result 402. As a non-limiting example, if the inferencing task is image classification, then the inferencing task result 804 can be a classification label that the pre-trained deep learning neural network 106 has generated for the previously-updated medical image 802. As another non-limiting example, if the inferencing task is image segmentation, then the inferencing task result 804 can be a pixel-wise or voxel-wise segmentation mask that the pre-trained deep learning neural network 106 has generated for the previously-updated medical image 802. As still another non-limiting example, if the inferencing task is image regression, then the inferencing task result 804 can be a regression result (e.g., denoised version, resolution-enhanced version, latent vector representation) that the pre-trained deep learning neural network 106 has generated for the previously-updated medical image 802.

Because the pre-trained deep learning neural network 106 can comprise the set of shallow layers 602 and the set of deep layers 604, execution of the pre-trained deep learning neural network 106 on the previously-updated medical image 802 can cause the previously-updated medical image 802 to pass through the set of shallow layers 602 and through the set of deep layers 604.

In various aspects, as the previously-updated medical image 802 passes through the set of shallow layers 602, the set of shallow layers 602 can produce a set of feature maps 806. Just like the set of feature maps 608 and the set of feature maps 704, the set of feature maps 806 can comprise a total of $f_{shallow}$ feature maps, where each of the set of feature maps 806 can have the same size, format, or dimensionality as a respective one of the set of feature maps 608 and thus also as a respective one of the set of feature maps 704. In various aspects, because the set of shallow layers 602 can be considered as being responsible for processing the visual style/texture of an inputted medical image, the set of feature maps 806 can be considered as representing, encoding, or otherwise being relevant to whatever visual style/texture that is exhibited by the previously-updated medical image 802.

Similarly, as the previously-updated medical image 802 passes through the set of deep layers 604, the set of deep layers 604 can produce a set of feature maps 808. Just like the set of feature maps 610 and the set of feature maps 706, the set of feature maps 808 can comprise a total of $f_{deep}$ feature maps, where each of the set of feature maps 808 can have the same size, format, or dimensionality as a respective one of the set of feature maps 610 and thus also as a respective one of the set of feature maps 706. In various instances, because the set of deep layers 604 can be considered as being responsible for processing the anatomical content of an inputted medical image, the set of feature maps 808 can be considered as representing, encoding, or otherwise being relevant to whatever anatomical content that is exhibited by the previously-updated medical image 802.

In various cases, the inferencing task result 804 can be considered as irrelevant for performing the in-situ style-transfer optimization algorithm 302. In contrast, the set of feature maps 806 and the set of feature maps 808 can, as described herein, be considered as relevant for performing the in-situ style-transfer optimization algorithm 302. Accordingly, the style-transfer component 114 can, in some cases, discard the inferencing task result 804, and the style-transfer component 114 can store, record, or otherwise preserve the set of feature maps 806 and the set of feature maps 808.

Figure 9:
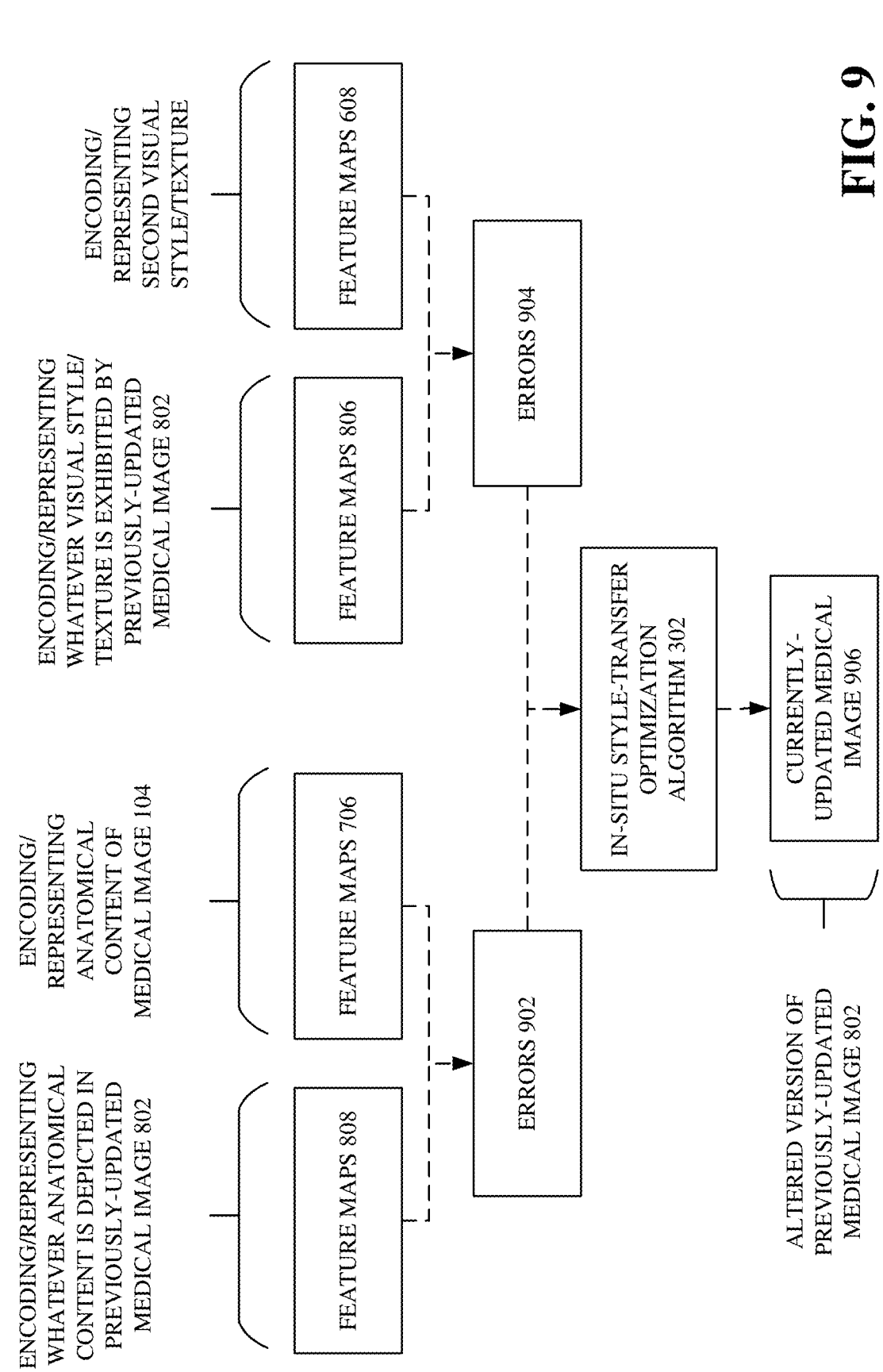

Now, consider FIG. 9. In various aspects, the style-transfer component 114 can electronically compute one or more errors 902 between the set of feature maps 808 and the set of feature maps 706. In various instances, any suitable error or loss computation techniques can be implemented. Non-limiting examples of such error or loss computation techniques can include MAE, MSE, or cross-entropy. In any case, because the set of feature maps 808 can be considered as representing, encoding, or otherwise being relevant to whatever anatomical content is depicted by the previously-updated medical image 802, and because the set of feature maps 706 can be considered as representing, encoding, or otherwise being relevant to whatever anatomical content is depicted by the medical image 104, the one or more errors 902 can be considered as indicating or otherwise representing how closely the anatomical content shown in the previously-updated medical image 802 matches that shown in the medical image 104.

Moreover, in various aspects, the style-transfer component 114 can electronically compute one or more errors 904 between the set of feature maps 806 and the set of feature maps 608. In various instances, any suitable error or loss computation techniques can be implemented. Non-limiting examples of such error or loss computation techniques can include MAE, MSE, or cross-entropy. In any case, because the set of feature maps 806 can be considered as representing, encoding, or otherwise being relevant to whatever visual style/texture is exhibited by the previously-updated medical image 802, and because the set of feature maps 608 can be considered as representing, encoding, or otherwise being relevant to the second visual style/texture, the one or more errors 904 can be considered as indicating or otherwise representing how closely the visual style/texture of the previously-updated medical image 802 matches the second visual style/texture.

In various aspects, the style-transfer component 114 can electronically feed the one or more errors 902 and the one or more errors 904 as input arguments into the objective function of the in-situ style-transfer optimization algorithm 302, and the style-transfer component 114 can accordingly execute or otherwise perform the in-situ style-transfer optimization algorithm 302. This can cause the style-transfer component 114 to change, modify, adjust, alter, or otherwise update the pixel values or voxel values of the previously-updated medical image 802, thereby yielding a currently-updated medical image 906. So, in various cases, the currently-updated medical image 906 can have the same format, size, or dimensionality as the previously-updated medical image 802 (and thus as the medical image 104), but the currently-updated medical image 906 can have different pixel values or different voxel values than the previously-updated medical image 802.

In any case, performance or execution of the in-situ style-transfer optimization algorithm 302 can cause the style-transfer component 114 to alter the pixel values or voxel values of the previously-updated medical image 802, so as to cause or otherwise correspond to an incremental and collective reduction in the one or more errors 902 and the one or more errors 904 (e.g., in the objective function that takes as arguments the one or more errors 902 and the one or more errors 904). In other words, the currently-updated medical image 906 can be considered as corresponding to an objective function magnitude that is smaller than that to which the previously-updated medical image 802 corresponded. Furthermore, during an immediately successive iteration of the in-situ style-transfer optimization algorithm 302, the currently-updated medical image 906 can be considered or otherwise treated as a new instance of the previously-updated medical image 802.

In various aspects, the style-transfer component 114 can repeat or otherwise iterate such execution and update procedure (e.g., can repeat or iterate FIGS. 8-9) any suitable number of times or otherwise until any suitable termination criterion is satisfied. As a non-limiting example, the style-transfer component 114 can iterate through FIGS. 8 and 9 until the objective function is below any suitable threshold value (e.g., until the one or more errors 902 and the one or more errors 904 are below any suitable respective threshold values).

In any case, there can be a final iteration, and whatever instance of the currently-updated medical image 906 that was produced during such final iteration (or that was otherwise most recently computed) can be considered or otherwise treated as the style-transferred medical image 304.

In other words, when the in-situ style-transfer optimization algorithm 302 is implemented as described with respect to FIGS. 6-9, the one or more errors 904 (and successive instances thereof in future iterations) can cause the in-situ style-transfer optimization algorithm 302 to accurately convert the first visual style/texture into the second visual style/texture. For this reason, the one or more errors 904 can be considered as representing one or more style/texture losses. In contrast, the one or more errors 902 (and successive instances thereof in future iterations) can cause the in-situ style-transfer optimization algorithm 302 to accurately preserve the anatomical content of the medical image 104. For this reason, the one or more errors 902 can be considered as representing one or more content losses.

Figure 10:
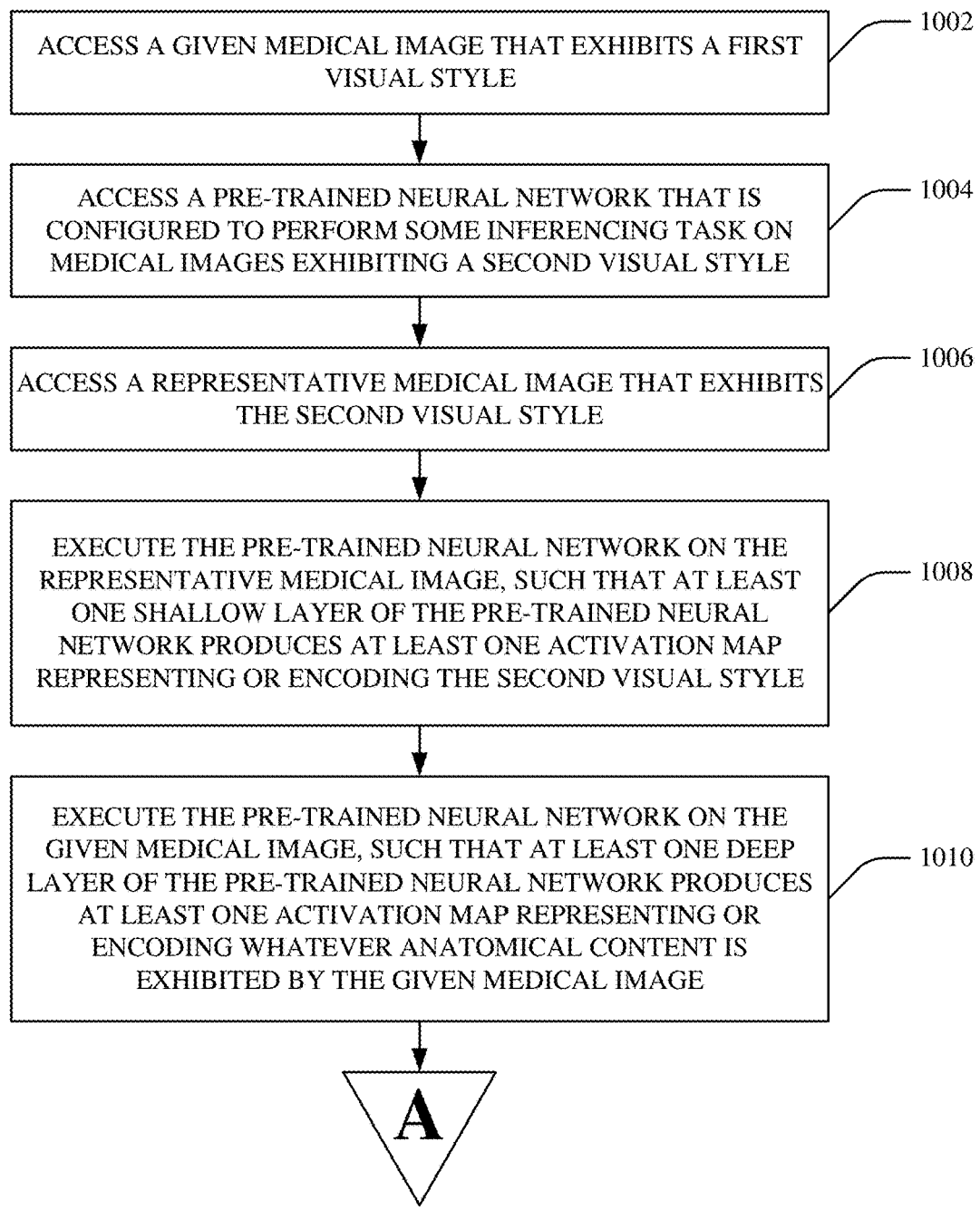
FIGS. 10-12 illustrate flow diagrams of example, non-limiting computer-implemented methods that facilitate implementation of an in-situ style-transfer optimization algorithm in accordance with one or more embodiments described herein.
Figure 11:
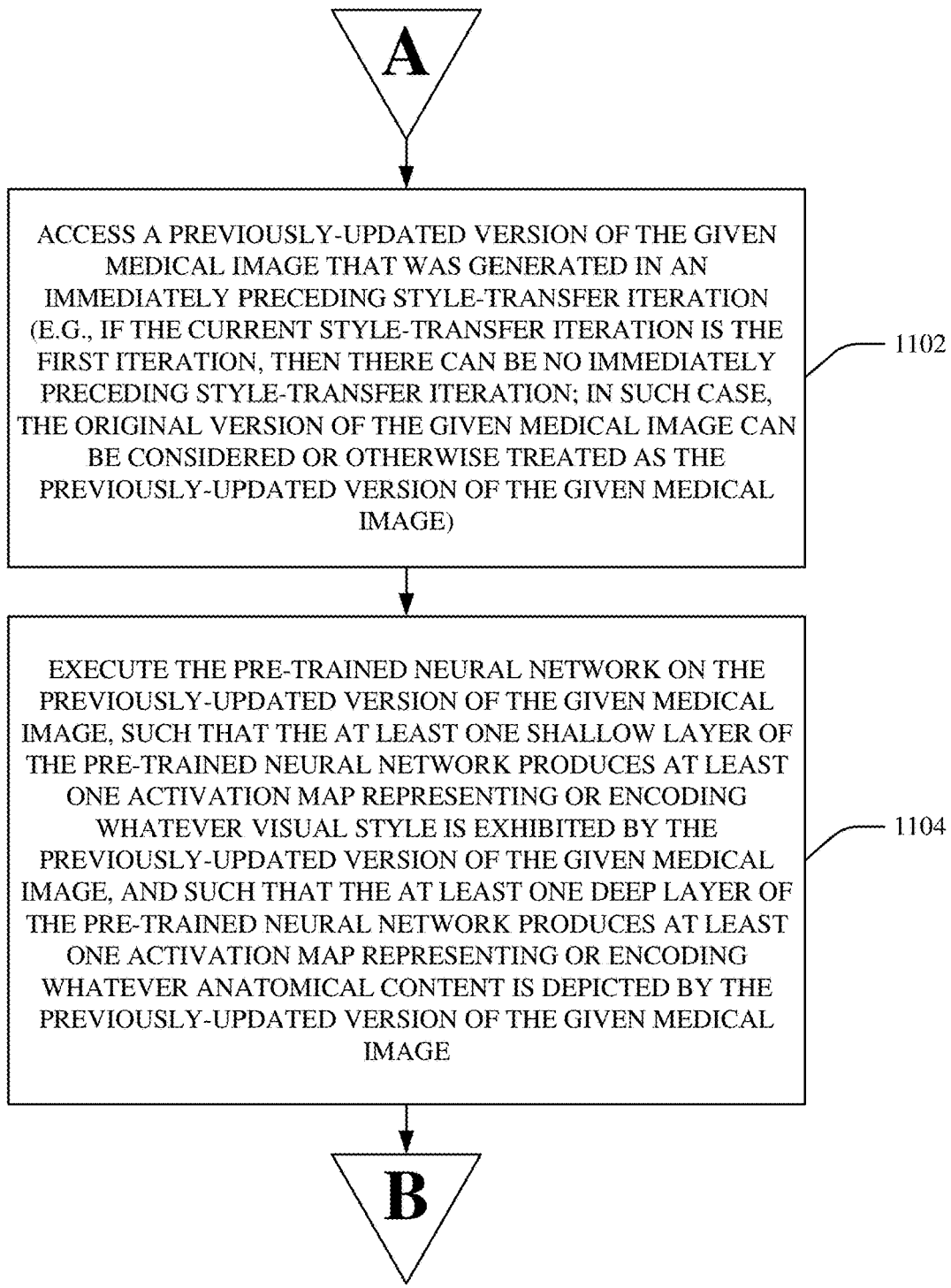
Figure 12:
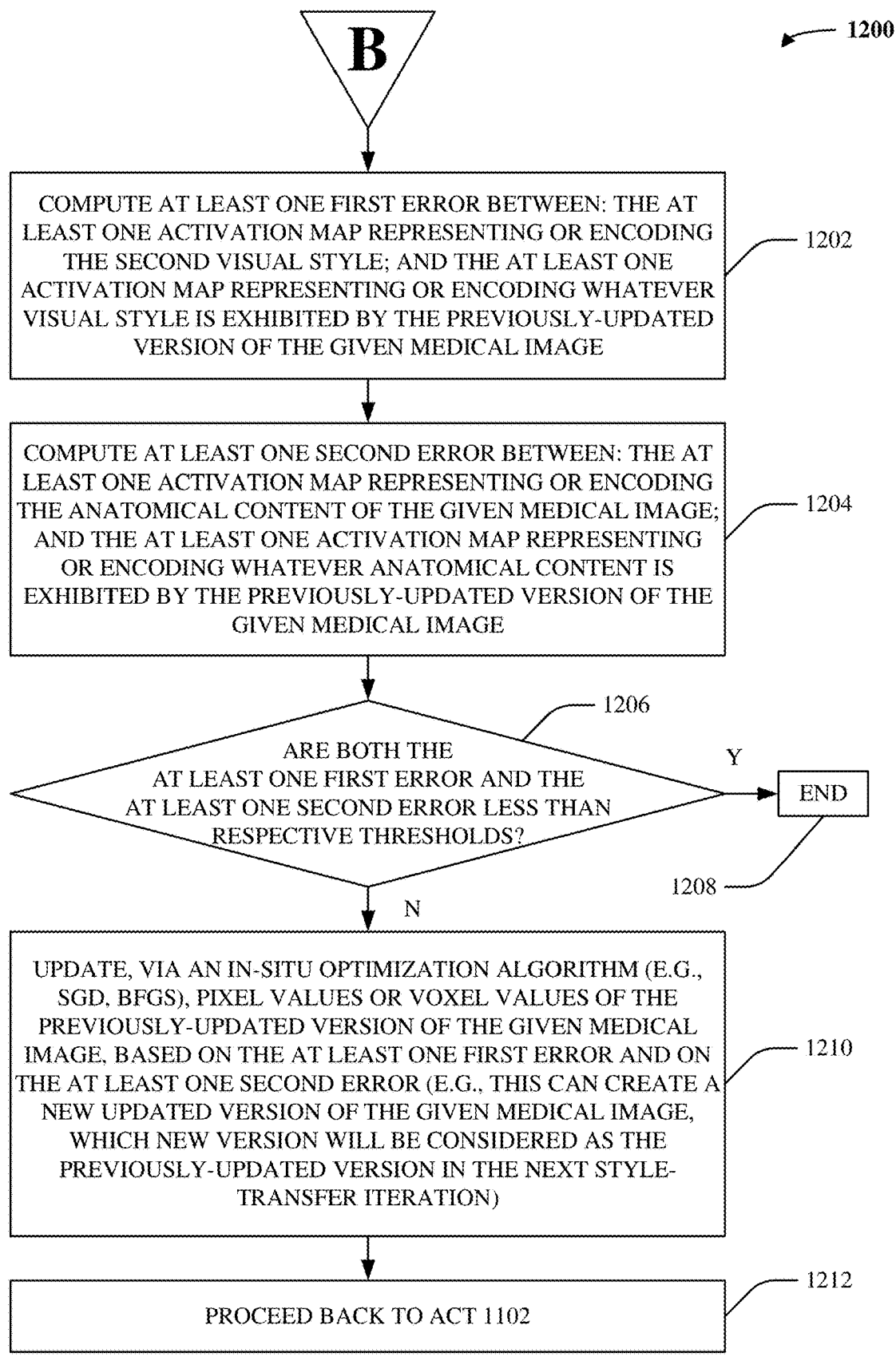

FIGS. 10-12 illustrate flow diagrams of example, non-limiting computer-implemented methods 1000, 1100, and 1200 that can facilitate implementation of the in-situ style-transfer optimization algorithm 302 in accordance with one or more embodiments described herein. In various cases, the style-transfer system 102 can facilitate the computer-implemented methods 1000, 1100, or 1200.

First, consider FIG. 10. In various embodiments, act 1002 can include accessing, by a device (e.g., via 112) operatively coupled to a processor (e.g., 108), a given medical image (e.g., 104) that exhibits a first visual style.

In various aspects, act 1004 can include accessing, by the device (e.g., via 112), a pre-trained neural network (e.g., 106) that is configured to perform some inferencing task (e.g., classification, segmentation, regression) on medical images exhibiting a second visual style.

In various instances, act 1006 can include accessing, by the device (e.g., via 112), a representative medical image (e.g., 118) that exhibits the second visual style.

In various cases, act 1008 can include executing, by the device (e.g., via 114), the pre-trained neural network on the representative medical image. This can cause at least one shallow layer (e.g., 602) of the pre-trained neural network to produce at least one activation map (e.g., 608) representing or encoding the second visual style.

In various aspects, act 1010 can include executing, by the device (e.g., via 114), the pre-trained neural network on the given medical image. This can cause at least one deep layer (e.g., 604) of the pre-trained neural network to produce at least one activation map (e.g., 706) representing or encoding whatever anatomical content is exhibited by the given medical image.

In various instances, the computer-implemented method 1000 can proceed to act 1102 of the computer-implemented method 1100.

As shown in FIG. 11, in various embodiments, act 1102 can include accessing, by the device (e.g., via 114), a previously-updated version (e.g., 802) of the given medical image, where such previously-updated version can have been generated in an immediately preceding style-transfer iteration. Note that, if a current style-transfer iteration is the very first style-transfer iteration, then there can be no immediately preceding style-transfer iteration. In such case, the original, unaltered version of the given medical image can be treated or otherwise considered as the previously-updated version of the given medical image.

In various aspects, act 1104 can include executing, by the device (e.g., via 114), the pre-trained neural network on the previously-updated version of the given medical image. In various instances, this can cause the at least one shallow layer of the pre-trained neural network to produce at least one activation map (e.g., 806) representing or encoding whatever visual style is exhibited by the previously-updated version of the given medical image. In various cases, this can also cause the at least one deep layer of the pre-trained neural network to produce at least one activation map (e.g., 808) representing or encoding whatever anatomical content is depicted by the previously-updated version of the given medical image.

In various aspects, the computer-implemented method 1100 can proceed to act 1202 of the computer-implemented method 1200.

As shown in FIG. 12, in various embodiments, act 1202 can include computing, by the device (e.g., via 114), at least one first error (e.g., 904) between: the at least one activation map representing or encoding the second visual style; and the at least one activation map representing or encoding whatever visual style is exhibited by the previously-updated version of the given medical image.

In various aspects, act 1204 can include computing, by the device (e.g., via 114), at least one second error (e.g., 902) between: the at least one activation map representing or encoding the anatomical content of the given medical image; and the at least one activation map representing or encoding whatever anatomical content is exhibited by the previously-updated version of the given medical image.

In various instances, act 1206 can include determining, by the device (e.g., via 114), whether both of the at least one first error and the at least one second error are less than respective thresholds. If so (e.g., if both the at least one first error and the at least one second error are under their respective thresholds), then the computer-implemented method 1200 can end at act 1208. If not (e.g., if either of the at least one first error or the at least one second error is not below its respective threshold), then the computer-implemented method 1200 can proceed to act 1210.

In various cases, act 1210 can include updating, by the device (e.g., via 114) and via an in-situ optimization algorithm (e.g., 302), pixel values or voxel values of the previously-updated version of the given medical image, based on the at least one first error and on the at least one second error. In various aspects, the in-situ optimization algorithm can include or otherwise be based on a stochastic gradient descent (SGD) technique or a Broyden-Fletcher-Goldfarb-Shanno (BFGS) technique. In various instances, such updating can create a new updated version (e.g., 906) of the given medical image, and such new updated version can be considered or otherwise serve as the previously-updated version in the next style-transfer iteration.

In various cases, act 1212 can include proceeding back to act 1102 of the computer-implemented method 1100. Accordingly, as can be seen, the computer-implemented methods 1100 and 1200 can iterate repeatedly until the at least one first error and the at least one second error are below their respective thresholds (e.g., determined at act 1206).

FIGS. 13-16 illustrate example, non-limiting experimental results in accordance with one or more embodiments described herein. More specifically, the present inventors reduced to practice a non-limiting example embodiment of the in-situ style-transfer optimization algorithm 302 and of the pre-trained deep learning neural network 106, and FIGS. 13-16 illustrate various experimental results produced by such non-limiting example embodiments. More specifically still, the non-limiting example embodiment of the pre-trained deep learning neural network 106 was configured to perform image segmentation on ultrasound images exhibiting a particular style/texture.

Figure 13:
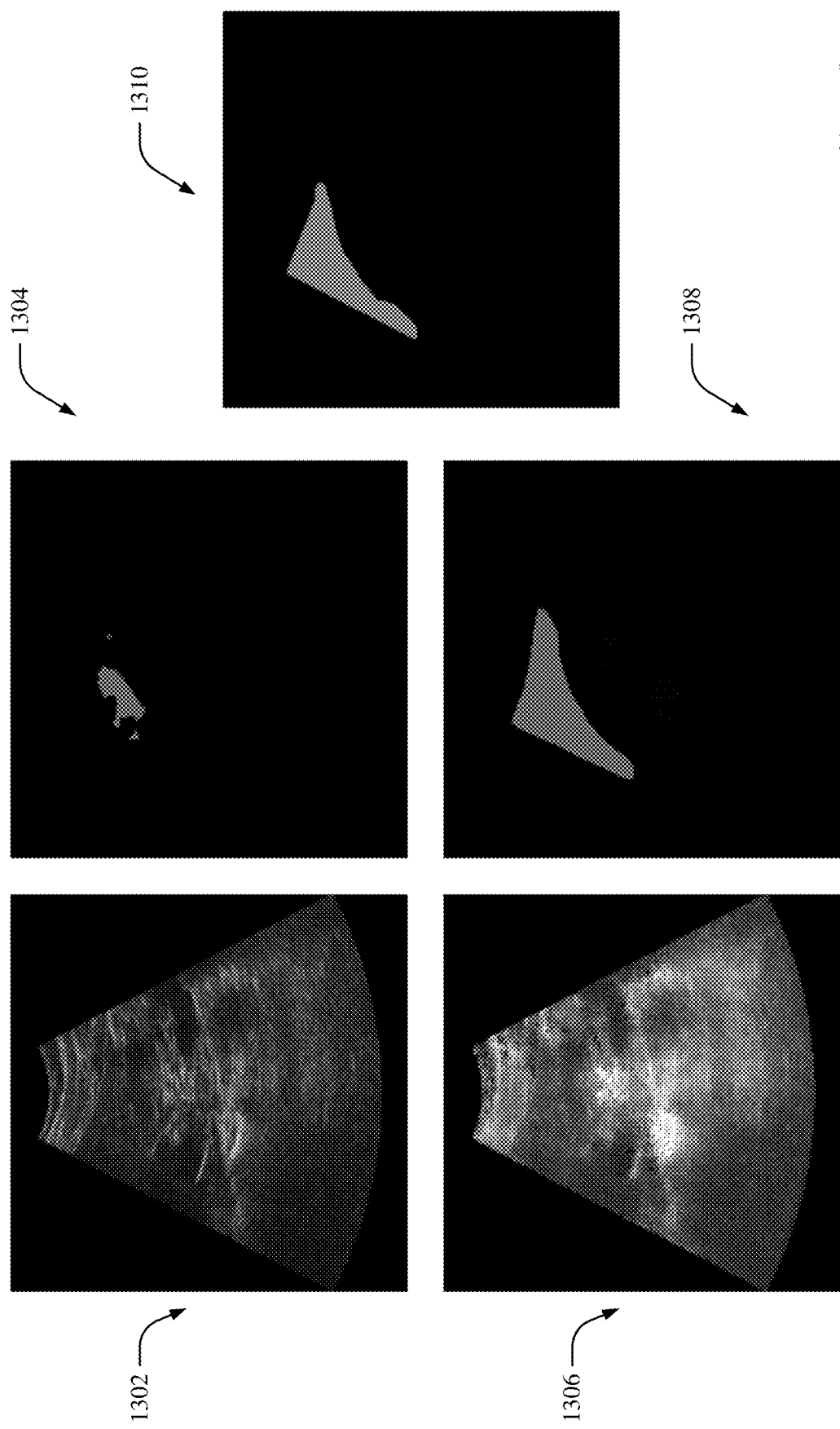
FIGS. 13-16 illustrate example, non-limiting experimental results in accordance with one or more embodiments described herein.

First, consider FIG. 13. As shown, FIG. 13 illustrates an ultrasound image 1302 exhibiting the first style/texture and a ground-truth segmentation mask 1310 that is known or deemed to correspond to the ultrasound image 1302. The non-limiting example embodiment of the pre-trained deep learning neural network 106 was executed on the ultrasound image 1302, thereby yielding a segmentation mask 1304. As can be seen, the segmentation mask 1304 does not closely match the ground-truth segmentation mask 1310. Indeed, the Dice-score between the segmentation mask 1304 and the ground-truth segmentation mask 1310 is 0.32273. In contrast, the non-limiting example embodiment of the in-situ style-transfer optimization algorithm 302 was iteratively executed on the ultrasound image 1302, thereby yielding a style-transferred ultrasound image 1306 that exhibits the second style/texture, and the non-limiting example embodiment of the pre-trained deep learning neural network 106 was executed on the style-transferred ultrasound image 1306, thereby yielding a segmentation mask 1308. As can be seen, the segmentation mask 1308 much more closely matches the ground-truth segmentation mask 1310. Indeed, the Dice-score between the segmentation mask 1308 and the ground-truth segmentation mask 1310 is 0.77219.

Figure 14:
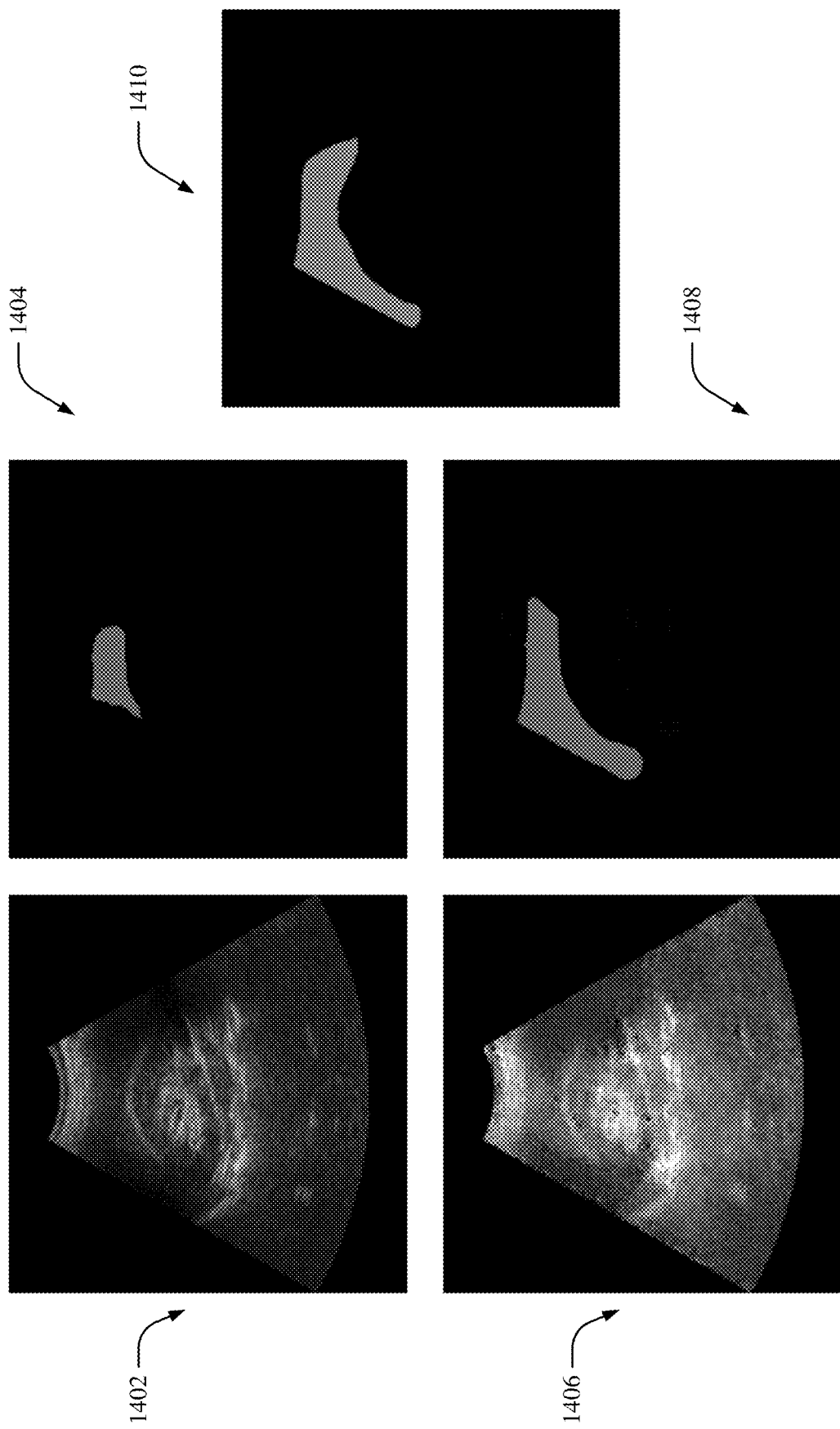

Next, consider FIG. 14. As shown, FIG. 14 illustrates an ultrasound image 1402 exhibiting the first style/texture and a ground-truth segmentation mask 1410 that is known or deemed to correspond to the ultrasound image 1402. The non-limiting example embodiment of the pre-trained deep learning neural network 106 was executed on the ultrasound image 1402, thereby yielding a segmentation mask 1404. As can be seen, the segmentation mask 1404 does not closely match the ground-truth segmentation mask 1410. Indeed, the Dice-score between the segmentation mask 1404 and the ground-truth segmentation mask 1410 is 0.476868. In contrast, the non-limiting example embodiment of the in-situ style-transfer optimization algorithm 302 was iteratively executed on the ultrasound image 1402, thereby yielding a style-transferred ultrasound image 1406 that exhibits the second style/texture, and the non-limiting example embodiment of the pre-trained deep learning neural network 106 was executed on the style-transferred ultrasound image 1406, thereby yielding a segmentation mask 1408. As can be seen, the segmentation mask 1408 much more closely matches the ground-truth segmentation mask 1410. Indeed, the Dice-score between the segmentation mask 1408 and the ground-truth segmentation mask 1410 is 0.827504.

Figure 15:
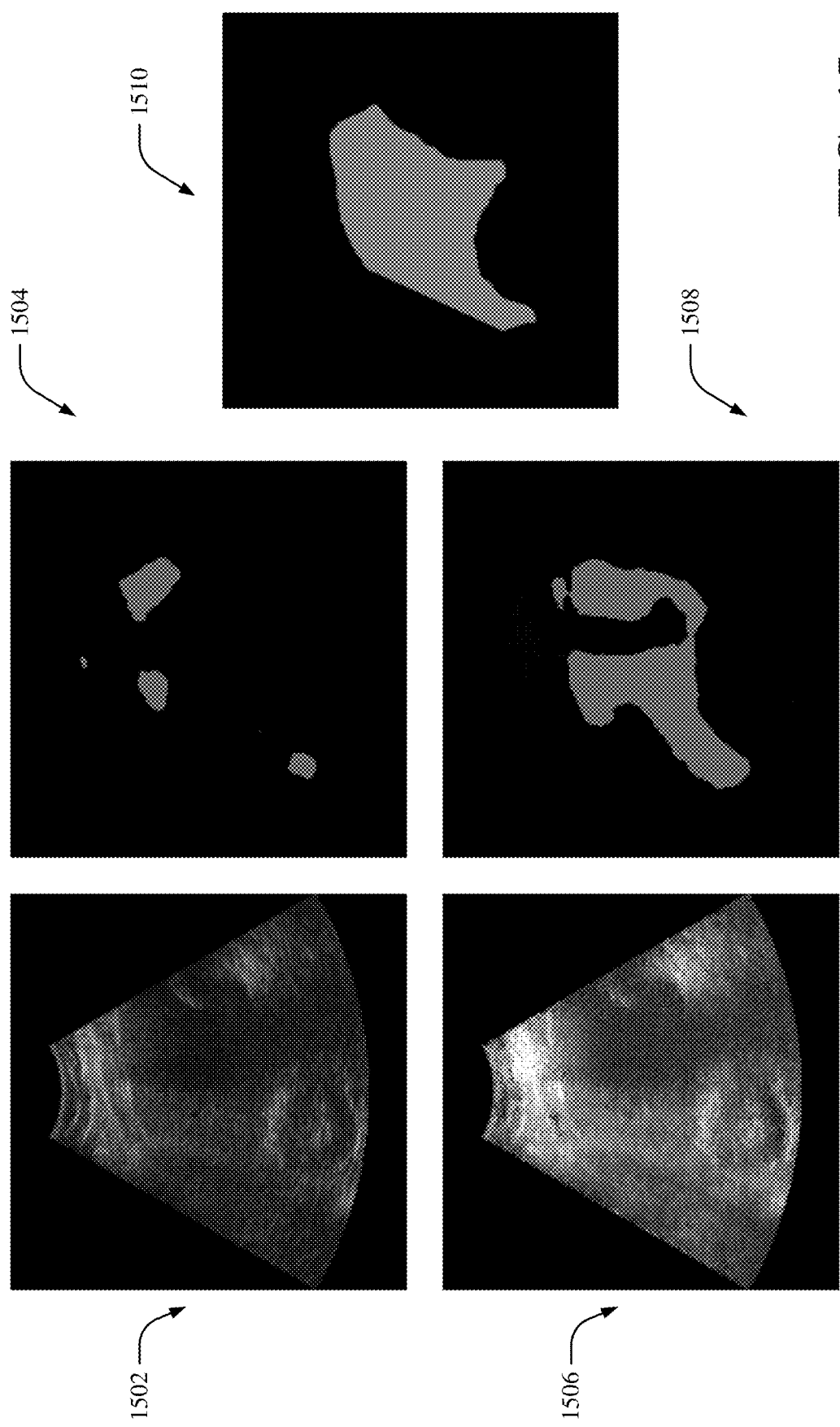

Now, consider FIG. 15. As shown, FIG. 15 illustrates an ultrasound image 1502 exhibiting the first style/texture and a ground-truth segmentation mask 1510 that is known or deemed to correspond to the ultrasound image 1502. The non-limiting example embodiment of the pre-trained deep learning neural network 106 was executed on the ultrasound image 1502, thereby yielding a segmentation mask 1504. As can be seen, the segmentation mask 1504 does not closely match the ground-truth segmentation mask 1510. Indeed, the Dice-score between the segmentation mask 1504 and the ground-truth segmentation mask 1510 is 0.255898. In contrast, the non-limiting example embodiment of the in-situ style-transfer optimization algorithm 302 was iteratively executed on the ultrasound image 1502, thereby yielding a style-transferred ultrasound image 1506 that exhibits the second style/texture, and the non-limiting example embodiment of the pre-trained deep learning neural network 106 was executed on the style-transferred ultrasound image 1506, thereby yielding a segmentation mask 1508. As can be seen, the segmentation mask 1508 much more closely matches the ground-truth segmentation mask 1510. Indeed, the Dice-score between the segmentation mask 1508 and the ground-truth segmentation mask 1510 is 0.718928.

Figure 16:
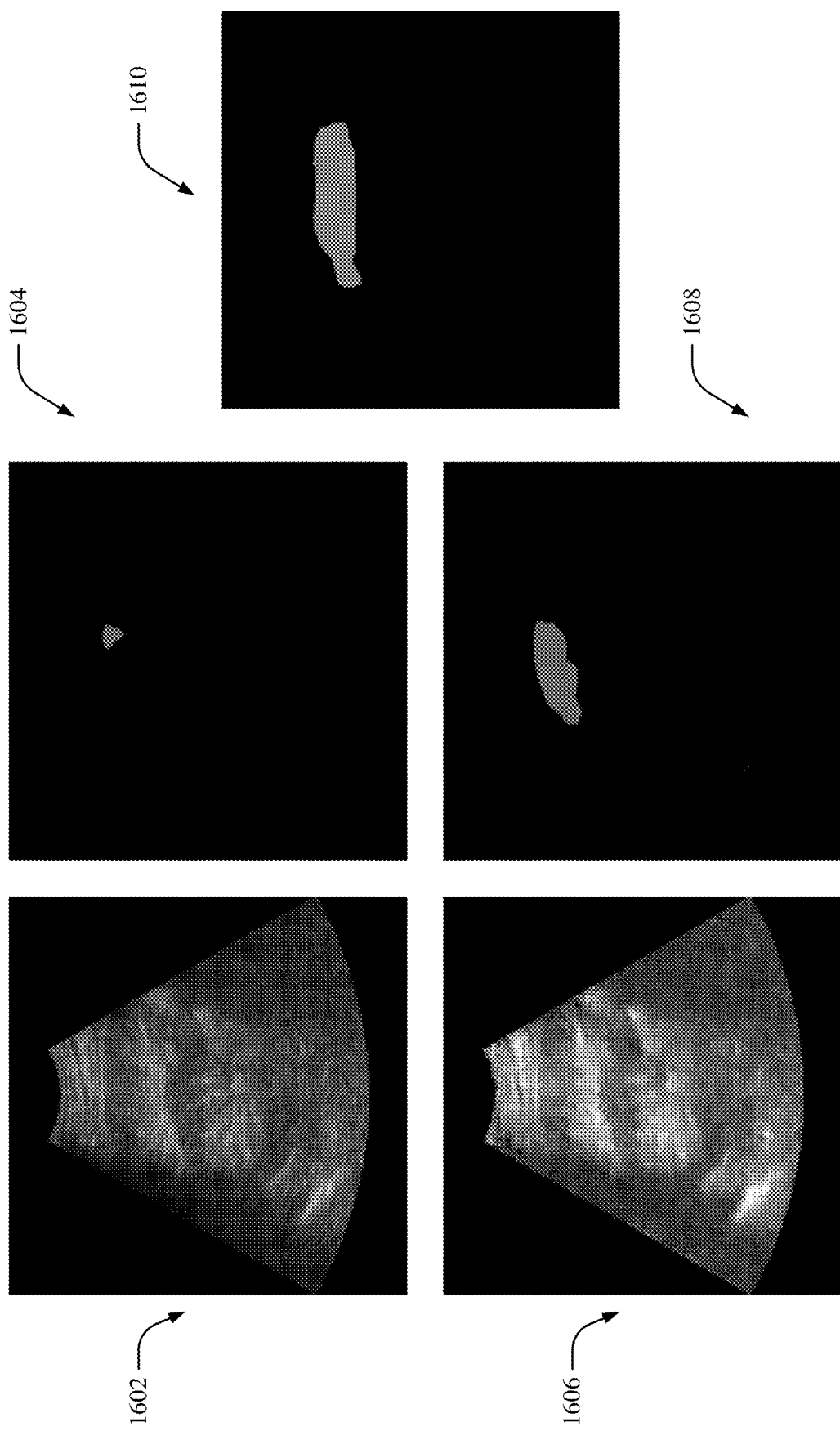

Lastly, consider FIG. 16. As shown, FIG. 16 illustrates an ultrasound image 1602 exhibiting the first style/texture and a ground-truth segmentation mask 1610 that is known or deemed to correspond to the ultrasound image 1602. The non-limiting example embodiment of the pre-trained deep learning neural network 106 was executed on the ultrasound image 1602, thereby yielding a segmentation mask 1604. As can be seen, the segmentation mask 1604 does not closely match the ground-truth segmentation mask 1610. Indeed, the Dice-score between the segmentation mask 1604 and the ground-truth segmentation mask 1610 is 0.103093. In contrast, the non-limiting example embodiment of the in-situ style-transfer optimization algorithm 302 was iteratively executed on the ultrasound image 1602, thereby yielding a style-transferred ultrasound image 1606 that exhibits the second style/texture, and the non-limiting example embodiment of the pre-trained deep learning neural network 106 was executed on the style-transferred ultrasound image 1606, thereby yielding a segmentation mask 1608. As can be seen, the segmentation mask 1608 much more closely matches the ground-truth segmentation mask 1610. Indeed, the Dice-score between the segmentation mask 1608 and the ground-truth segmentation mask 1610 is 0.647106.

Figure 17:
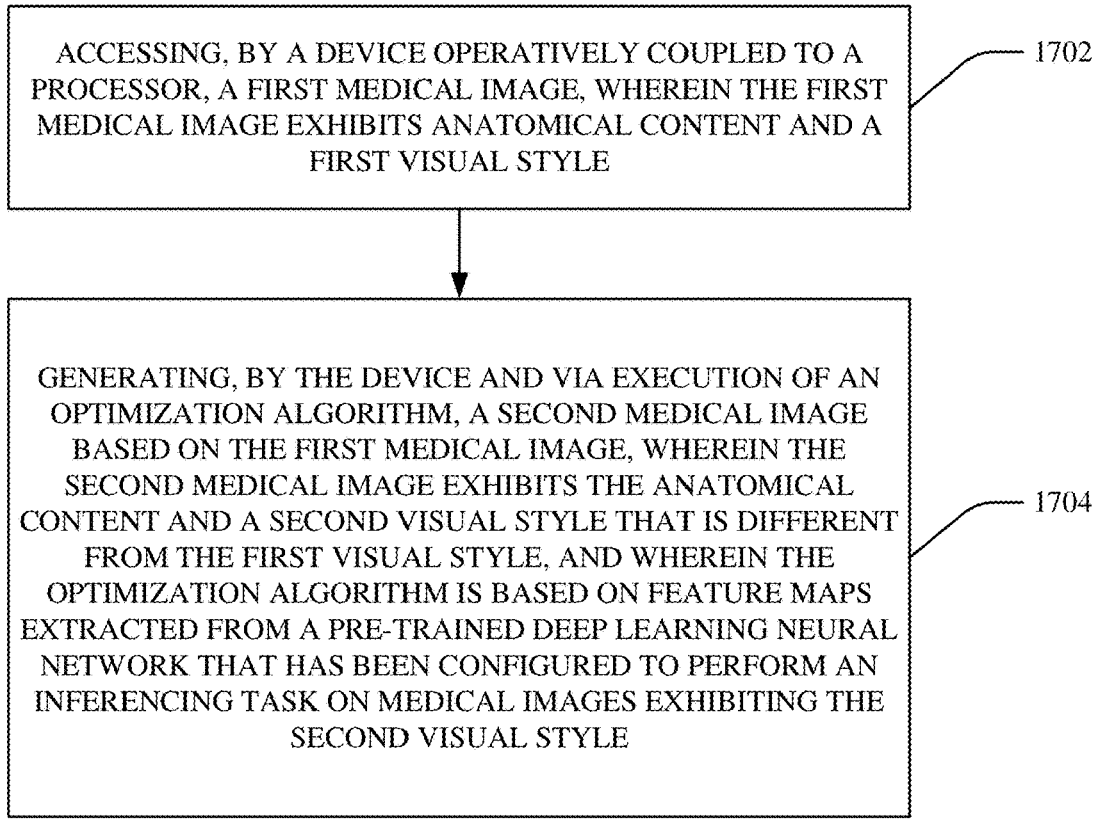
FIG. 17 illustrates a flow diagram of an example, non-limiting computer-implemented method that facilitates task-specific image style transfer in accordance with one or more embodiments described herein.

FIG. 17 illustrates a flow diagram of an example, non-limiting computer-implemented method 1700 that can facilitate task-specific image style transfer in accordance with one or more embodiments described herein. In various cases, the style-transfer system 102 can facilitate the computer-implemented method 1700.

In various embodiments, act 1702 can include accessing, by a device (e.g., via 112) operatively coupled to a processor (e.g., 108), a first medical image (e.g., 104), wherein the first medical image can exhibit anatomical content and a first visual style.

In various aspects, act 1704 can include generating, by the device (e.g., via 114) and via execution of an optimization algorithm (e.g., 302), a second medical image (e.g., 304) based on the first medical image, wherein the second medical image can exhibit the anatomical content and a second visual style that is different from the first visual style, and wherein the optimization algorithm can be based on feature maps (e.g., 608, 706, 806, 808) extracted from a pre-trained deep learning neural network (e.g., 106) that has been configured to perform an inferencing task on medical images exhibiting the second visual style.

Although not explicitly shown in FIG. 17, the device can iteratively execute the optimization algorithm on the first medical image, based on losses (e.g., 902, 904) defined by the feature maps extracted from the pre-trained deep learning neural network, and the second medical image can be outputted by the optimization algorithm during a final iteration of such iterative execution.

Although not explicitly shown in FIG. 17, the computer-implemented method 1700 can comprise: accessing, by the device (e.g., via 114) and during a current iteration of such iterative execution, an updated version (e.g., 802) of the first medical image that was produced by the optimization algorithm during a preceding iteration of such iterative execution; executing, by the device (e.g., via 114) and during the current iteration, the pre-trained deep learning neural network on the updated version of the first medical image, wherein one or more shallow layers (e.g., 602) of the pre-trained deep learning neural network produce one or more first feature maps (e.g., 806) based on the updated version of the first medical image, and wherein one or more deep layers (e.g., 604) of the pre-trained deep learning neural network produce one or more second feature maps (e.g., 808) based on the updated version of the first medical image; executing, by the device (e.g., via 114), the pre-trained deep learning neural network on a representative medical image (e.g., 118) that exhibits the second visual style, wherein the one or more shallow layers of the pre-trained deep learning neural network produce one or more third feature maps (e.g., 608) based on the representative medical image; executing, by the device (e.g., via 114), the pre-trained deep learning neural network on the first medical image, wherein the one or more deep layers of the pre-trained deep learning neural network produce one or more fourth feature maps (e.g., 706) based on the first medical image; and updating, by the device (e.g., via 114), during the current iteration, and via execution of the optimization algorithm, pixel values or voxel values of the updated version of the first medical image, based on first errors (e.g., 904) between the one or more first feature maps and the one or more third feature maps, and based on second errors (e.g., 902) between the one or more second feature maps and the one or more fourth feature maps, thereby yielding another updated version (e.g., 906) of the first medical image.

Although not explicitly shown in FIG. 17, the computer-implemented method 1700 can comprise: executing, by the device (e.g., via 116), the pre-trained deep learning neural network (e.g., 106) on the second medical image (e.g., 304).

Although not explicitly shown in FIG. 17, the computer-implemented method 1700 can comprise: rendering, by the device (e.g., via 116), the second medical image (e.g., 304) on an electronic display.

Although not explicitly shown in FIG. 17, the inferencing task can be image segmentation, image classification, or image regression.

Although not explicitly shown in FIG. 17, the first visual style can correspond to a first medical imaging modality (e.g., ultrasound scanner), and the second visual style can correspond to a second medical imaging modality (e.g., CT scanner) that is different from the first medical imaging modality; or the first visual style can correspond to first settings of the first medical imaging modality (e.g., an ultrasound scanner operating at a particular voltage or focal spot size), and the second visual style can correspond to second settings of the first medical imaging modality that are different from the first settings (e.g., that same ultrasound scanner operating at a different voltage or focal spot size).

In various embodiments, a computer program product for facilitating task-specific image style transfer can be provided. In various aspects, the computer program product can comprise a non-transitory computer-readable memory (e.g., 110) having program instructions embodied therewith. In various instances, the program instructions can be executable by a processor (e.g., 108) to cause the processor to: access a medical image (e.g., 104) exhibiting a visual texture; iteratively execute an optimization algorithm (e.g., 302) on the medical image, thereby yielding a style-transferred version (e.g., 304) of the medical image that exhibits a different visual texture, wherein the optimization algorithm can be driven by hidden layer activations (e.g., 608, 706, 806, 808) extracted from a neural network (e.g., 106), and wherein the neural network can have been pre-trained to operate on medical images exhibiting the different visual texture; and execute the neural network on the style-transferred version of the medical image.

In various aspects, the program instructions can be further executable to cause the processor to: access, during a current iteration, an updated version (e.g., 802) of the medical image that was produced by the optimization algorithm during a prior iteration; execute, during the current iteration, the neural network on the updated version of the medical image, wherein a shallow layer (e.g., 602) of the neural network produces a first activation map (e.g., 806) based on the updated version of the medical image, and wherein a deep layer (e.g., 604) of the neural network produces a second activation map (e.g., 808) based on the updated version of the medical image; execute the neural network on a representative medical image (e.g., 118) exhibiting the different visual texture, wherein the shallow layer of the neural network produces a third activation map (e.g., 608) based on the representative medical image; and execute the neural network on the medical image, wherein the deep layer of the neural network produces a fourth activation map (e.g., 706) based on the medical image.

In various cases, the program instructions can be further executable to cause the processor to: update, via execution of the optimization algorithm, pixel values or voxel values of the updated version of the medical image, wherein the optimization algorithm can be based on a first error (e.g., 904) between the first activation map and the third activation map and can also be based on a second error (e.g., 902) between the second activation map and the fourth activation map.

In various aspects, the optimization algorithm can be a stochastic gradient descent algorithm or a Broyden-Fletcher-Goldfarb-Shanno algorithm.

In various aspects, the neural network can have been pre-trained to perform an inferencing task (e.g., classification, segmentation, regression) on medical images exhibiting the different visual texture, such that the style-transferred version of the medical image can be considered as being tailored or specific to the inferencing task.

In various instances, the visual texture and the different visual texture can correspond to different controllable settings of a medical imaging modality.

Although the herein disclosure mainly describes various embodiments as applying to medical images (e.g., 104, 118), this is a mere non-limiting example. Various embodiments described herein can be implemented to perform improved image style transfer on any suitable type of images (e.g., on non-medical images).

Although the herein disclosure mainly describes various embodiments as pertaining to a deep learning neural network (e.g., 106), this is a mere non-limiting example. In various aspects, the herein-described teachings can be applied to any suitable machine learning models exhibiting any suitable artificial intelligence architectures (e.g., support vector machines, naïve Bayes, linear regression, logistic regression, decision trees, random forest).

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, z_n)$, to a confidence that the input belongs to a class, as by $f(z)=confidence(class)$. Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

The herein disclosure describes non-limiting examples. For case of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

Figure 18:
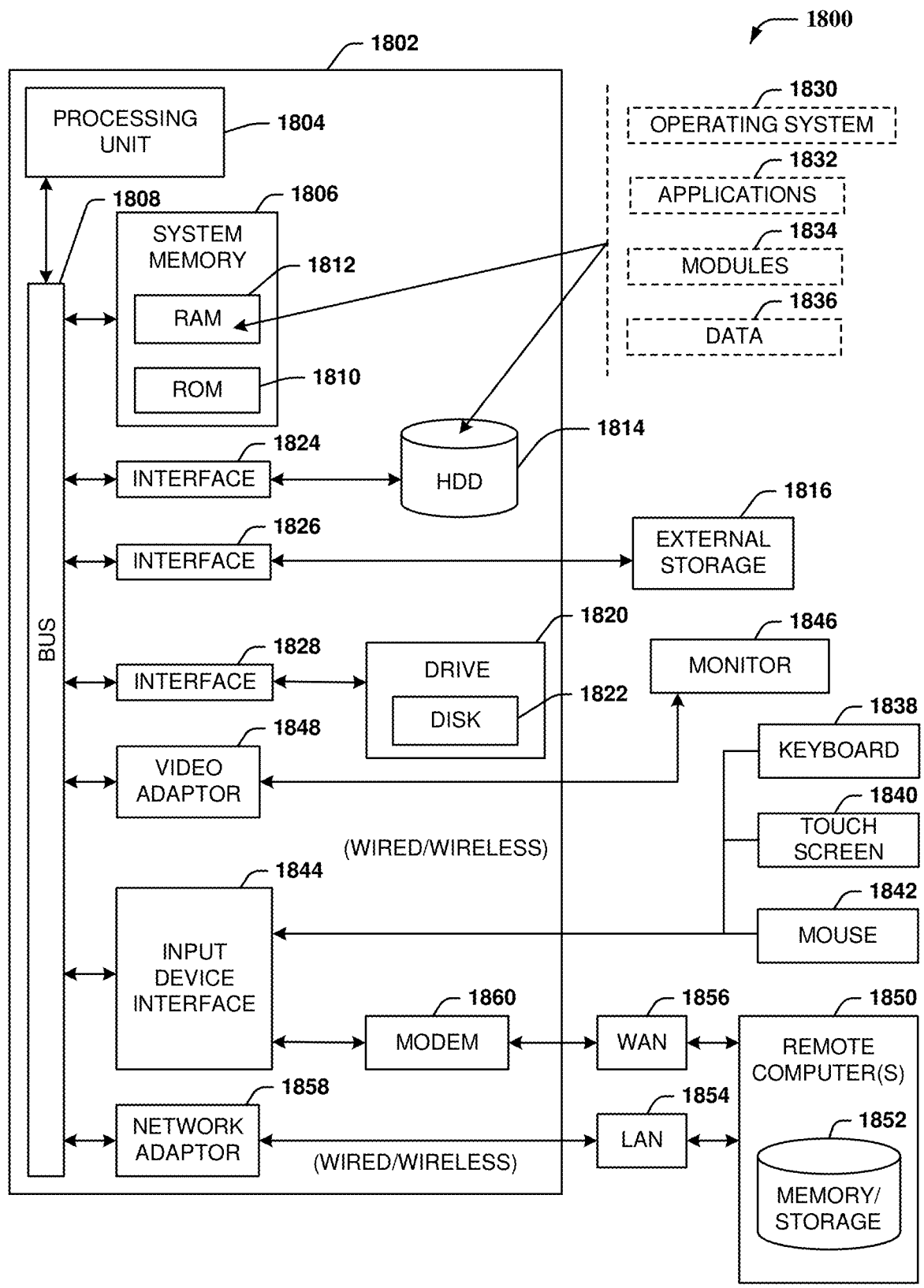
FIG. 18 illustrates a block diagram of an example, non-limiting operating environment in which one or more embodiments described herein can be facilitated.

In order to provide additional context for various embodiments described herein, FIG. 18 and the following discussion are intended to provide a brief, general description of a suitable computing environment 1800 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IOT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 18, the example environment 1800 for implementing various embodiments of the aspects described herein includes a computer 1802, the computer 1802 including a processing unit 1804, a system memory 1806 and a system bus 1808. The system bus 1808 couples system components including, but not limited to, the system memory 1806 to the processing unit 1804. The processing unit 1804 can be any of various commercially available processors. Dual microprocessors and other multi-processor architectures can also be employed as the processing unit 1804.

The system bus 1808 can be any of several types of bus structure that can further interconnect to a memory bus (with or without a memory controller), a peripheral bus, and a local bus using any of a variety of commercially available bus architectures. The system memory 1806 includes ROM 1810 and RAM 1812. A basic input/output system (BIOS) can be stored in a non-volatile memory such as ROM, erasable programmable read only memory (EPROM), EEPROM, which BIOS contains the basic routines that help to transfer information between elements within the computer 1802, such as during startup. The RAM 1812 can also include a high-speed RAM such as static RAM for caching data.

The computer 1802 further includes an internal hard disk drive (HDD) 1814 (e.g., EIDE, SATA), one or more external storage devices 1816 (e.g., a magnetic floppy disk drive (FDD) 1816, a memory stick or flash drive reader, a memory card reader, etc.) and a drive 1820, e.g., such as a solid state drive, an optical disk drive, which can read or write from a disk 1822, such as a CD-ROM disc, a DVD, a BD, etc. Alternatively, where a solid state drive is involved, disk 1822 would not be included, unless separate. While the internal HDD 1814 is illustrated as located within the computer 1802, the internal HDD 1814 can also be configured for external use in a suitable chassis (not shown). Additionally, while not shown in environment 1800, a solid state drive (SSD) could be used in addition to, or in place of, an HDD 1814. The HDD 1814, external storage device(s) 1816 and drive 1820 can be connected to the system bus 1808 by an HDD interface 1824, an external storage interface 1826 and a drive interface 1828, respectively. The interface 1824 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1802, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1812, including an operating system 1830, one or more application programs 1832, other program modules 1834 and program data 1836. All or portions of the operating system, applications, modules, or data can also be cached in the RAM 1812. The systems and methods described herein can be implemented utilizing various commercially available operating systems or combinations of operating systems.

Computer 1802 can optionally comprise emulation technologies. For example, a hypervisor (not shown) or other intermediary can emulate a hardware environment for operating system 1830, and the emulated hardware can optionally be different from the hardware illustrated in FIG. 18. In such an embodiment, operating system 1830 can comprise one virtual machine (VM) of multiple VMs hosted at computer 1802. Furthermore, operating system 1830 can provide runtime environments, such as the Java runtime environment or the .NET framework, for applications 1832. Runtime environments are consistent execution environments that allow applications 1832 to run on any operating system that includes the runtime environment. Similarly, operating system 1830 can support containers, and applications 1832 can be in the form of containers, which are lightweight, standalone, executable packages of software that include, e.g., code, runtime, system tools, system libraries and settings for an application.

Further, computer 1802 can be enable with a security module, such as a trusted processing module (TPM). For instance with a TPM, boot components hash next in time boot components, and wait for a match of results to secured values, before loading a next boot component. This process can take place at any layer in the code execution stack of computer 1802, e.g., applied at the application execution level or at the operating system (OS) kernel level, thereby enabling security at any level of code execution.

A user can enter commands and information into the computer 1802 through one or more wired/wireless input devices, e.g., a keyboard 1838, a touch screen 1840, and a pointing device, such as a mouse 1842. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1804 through an input device interface 1844 that can be coupled to the system bus 1808, but can be connected by other interfaces, such as a parallel port, an IEEE 1394 serial port, a game port, a USB port, an IR interface, a BLUETOOTH® interface, etc.

A monitor 1846 or other type of display device can be also connected to the system bus 1808 via an interface, such as a video adapter 1848. In addition to the monitor 1846, a computer typically includes other peripheral output devices (not shown), such as speakers, printers, etc.

The computer 1802 can operate in a networked environment using logical connections via wired or wireless communications to one or more remote computers, such as a remote computer(s) 1850. The remote computer(s) 1850 can be a workstation, a server computer, a router, a personal computer, portable computer, microprocessor-based entertainment appliance, a peer device or other common network node, and typically includes many or all of the elements described relative to the computer 1802, although, for purposes of brevity, only a memory/storage device 1852 is illustrated. The logical connections depicted include wired/wireless connectivity to a local area network (LAN) 1854 or larger networks, e.g., a wide area network (WAN) 1856. Such LAN and WAN networking environments are commonplace in offices and companies, and facilitate enterprise-wide computer networks, such as intranets, all of which can connect to a global communications network, e.g., the Internet.

When used in a LAN networking environment, the computer 1802 can be connected to the local network 1854 through a wired or wireless communication network interface or adapter 1858. The adapter 1858 can facilitate wired or wireless communication to the LAN 1854, which can also include a wireless access point (AP) disposed thereon for communicating with the adapter 1858 in a wireless mode.

When used in a WAN networking environment, the computer 1802 can include a modem 1860 or can be connected to a communications server on the WAN 1856 via other means for establishing communications over the WAN 1856, such as by way of the Internet. The modem 1860, which can be internal or external and a wired or wireless device, can be connected to the system bus 1808 via the input device interface 1844. In a networked environment, program modules depicted relative to the computer 1802 or portions thereof, can be stored in the remote memory/storage device 1852. It will be appreciated that the network connections shown are example and other means of establishing a communications link between the computers can be used.

When used in either a LAN or WAN networking environment, the computer 1802 can access cloud storage systems or other network-based storage systems in addition to, or in place of, external storage devices 1816 as described above, such as but not limited to a network virtual machine providing one or more aspects of storage or processing of information. Generally, a connection between the computer 1802 and a cloud storage system can be established over a LAN 1854 or WAN 1856 e.g., by the adapter 1858 or modem 1860, respectively. Upon connecting the computer 1802 to an associated cloud storage system, the external storage interface 1826 can, with the aid of the adapter 1858 or modem 1860, manage storage provided by the cloud storage system as it would other types of external storage. For instance, the external storage interface 1826 can be configured to provide access to cloud storage sources as if those sources were physically connected to the computer 1802.

The computer 1802 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 19:
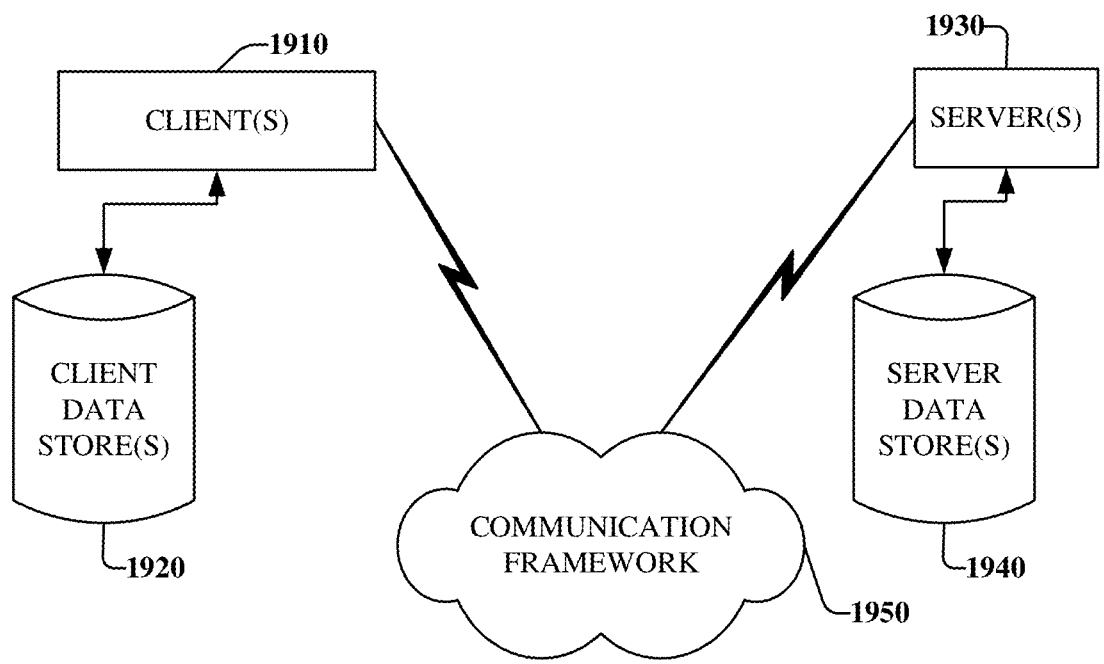
FIG. 19 illustrates an example networking environment operable to execute various implementations described herein.

FIG. 19 is a schematic block diagram of a sample computing environment 1900 with which the disclosed subject matter can interact. The sample computing environment 1900 includes one or more client(s) 1910. The client(s) 1910 can be hardware or software (e.g., threads, processes, computing devices). The sample computing environment 1900 also includes one or more server(s) 1930. The server(s) 1930 can also be hardware or software (e.g., threads, processes, computing devices). The servers 1930 can house threads to perform transformations by employing one or more embodiments as described herein, for example. One possible communication between a client 1910 and a server 1930 can be in the form of a data packet adapted to be transmitted between two or more computer processes. The sample computing environment 1900 includes a communication framework 1950 that can be employed to facilitate communications between the client(s) 1910 and the server(s) 1930. The client(s) 1910 are operably connected to one or more client data store(s) 1920 that can be employed to store information local to the client(s) 1910. Similarly, the server(s) 1930 are operably connected to one or more server data store(s) 1940 that can be employed to store information local to the servers 1930.

The present invention may be a system, a method, an apparatus or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations or block diagrams of methods, apparatus (systems), and computer program products according to embodiments of the invention. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory configured to store computer-executable components; and
a processor that executes at least one of the computer-executable components that:
accesses a first medical image that exhibits first anatomical content and a first visual style; and
generates, via execution of an optimization algorithm, a second medical image based on the first medical image, wherein the second medical image exhibits the anatomical content and a second visual style that is different from the first visual style, wherein the optimization algorithm is based on feature maps extracted from a pre-trained deep learning neural network that has been configured to perform an inferencing task on medical images exhibiting the second visual style, wherein the pre-trained deep learning neural network comprises at least one shallow layer and at least one deep layer, and wherein executing the optimization algorithm comprises:
  executing the pre-trained deep learning neural network on a representative medical image that exhibits the second visual style, wherein the pre-trained deep learning neural network produces, based on the representative medical image, at least one first shallow feature map via the at least one shallow layer, and at least one first deep feature map via the at least one deep layer; and
  iteratively performs until the second medical image is generated:
    wherein a first iteration comprises:
      executing the pre-trained deep learning neural network on the first medical image that exhibits the first visual style, wherein the pre-trained deep learning neural network produces, based on the first medical image, at least one second shallow feature map via the at least one shallow layer, and at least one second deep feature map via the at least one deep layer, and
      generating an updated first medical image based on at least one first error between the at least one first shallow feature map;
    and the at least one second shallow feature map;
    wherein subsequent iterations to the first iteration comprise:
      executing, during a current iteration of the subsequent iterations, the pre-trained deep learning neural network on the updated first medical image from an immediately preceding iteration to the current iteration, wherein the pre-trained deep learning neural network produces, based on the updated first medical image from the immediately preceding iteration, at least one third deep feature map via the at least one deep layer, and at least one third shallow feature map via the at least one shallow layer,
      generating the updated first medical image for the current iteration based on at least one second error between the at least one first shallow feature map and the at least one third shallow feature map, and further based on at least one third error between the at least one second deep feature map and the at least one third deep feature map,
      in response to an objective function associated with the at least one second error and the at least one third error satisfying a defined criterion, using the updated first medical image for the current iteration as the second medical image.

2. The system of claim 1, wherein generating the updated first medical image for the current iteration comprises updating at least one of pixel values or voxel values of the updated first medical image from the immediately preceding iteration based on the at least one second error and the at least one third error.

3. The system of claim 1, wherein the at least one shallow layer is associated with processing visual styles.

4. The system of claim 1, wherein the at least one of the computer-executable components further:
  renders the second medical image on an electronic display.

5. The system of claim 1, wherein the inferencing task comprises at least one of image segmentation, image classification, or image regression.

6. The system of claim 1, wherein:
  the first visual style corresponds to a first medical imaging modality, and the second visual style corresponds to a second medical imaging modality that is different from the first medical imaging modality; or
  the first visual style corresponds to first settings of the first medical imaging modality, and the second visual style corresponds to second settings of the first medical imaging modality that are different from the first settings.

7. The system of claim 1, wherein the at least one deep layer is associated with processing anatomical contents.

8. A computer-implemented method, comprising:
  accessing, by a device operatively coupled to a processor, a first medical image that exhibits first anatomical content and a first visual style; and
  generating, by the device, via execution of an optimization algorithm, a second medical image based on the first medical image, wherein the second medical image exhibits the anatomical content and a second visual style that is different from the first visual style, and wherein the optimization algorithm is based on feature maps extracted from a pre-trained deep learning neural network that has been configured to perform an inferencing task on medical images exhibiting the second visual style, wherein the pre-trained deep learning neural network comprises at least one shallow layer and at least one deep layer, and wherein executing the optimization algorithm comprises:
    executing the pre-trained deep learning neural network on a representative medical image that exhibits the second visual style, wherein the pre-trained deep learning neural network produces, based on the representative medical image, at least one first shallow feature map via the at least one shallow layer, and at least one first deep feature map via the at least one deep layer; and
    iteratively performs until the second medical image is generated:
      wherein a first iteration comprises:
        executing the pre-trained deep learning neural network on the first medical image that exhibits the first visual style, wherein the pre-trained deep learning neural network produces, based on the first medical image, at least one second shallow feature map via the at least one shallow layer, and at least one second deep feature map via the at least one deep layer, and
        generating an updated first medical image based on at least one first error between the at least one first shallow feature map; and the at least one second shallow feature map;
      wherein subsequent iterations to the first iteration comprise:
        executing, during a current iteration of the subsequent iterations, the pre-trained deep learning neural network on the updated first medical image from an immediately preceding iteration to the current iteration, wherein the pre-trained deep learning neural network produces, based on the updated first medical image from the immediately preceding iteration, at least one third deep feature map via the at least one deep layer, and at least one third shallow feature map via the at least one shallow layer, generating the updated first medical image for the current iteration based on at least one second error between the at least one first shallow feature map and the at least one third shallow feature map, and further based on at least one third error between the at least one second deep feature map and the at least one third deep feature map, in response to an objective function associated with the at least one second error and the at least one third error satisfying a defined criterion, using the updated first medical image for the current iteration as the second medical image.

9. The computer-implemented method of claim 8, wherein generating the updated first medical image for the current iteration comprises updating at least one of pixel values or voxel values of the updated first medical image from the immediately preceding iteration based on the at least one second error and the at least one third error.

10. The computer-implemented method of claim 8, wherein the at least one shallow layer is associated with processing visual styles.

11. The computer-implemented method of claim 8, further comprising:
rendering, by the device, the second medical image on an electronic display.

12. The computer-implemented method of claim 8, wherein the inferencing task comprises at least one of image segmentation, image classification, or image regression.

13. The computer-implemented method of claim 8, wherein:
the first visual style corresponds to a first medical imaging modality, and the second visual style corresponds to a second medical imaging modality that is different from the first medical imaging modality; or
the first visual style corresponds to first settings of the first medical imaging modality, and the second visual style corresponds to second settings of the first medical imaging modality that are different from the first settings.

14. The computer-implemented method of claim 8, wherein the at least one deep layer is associated with processing anatomical contents.

15. A computer program product for facilitating task-specific image style transfer, the computer program product comprising a non-transitory computer-readable memory having program instructions embodied therewith, the program instructions executable by a processor to cause the processor to:
access a first medical image that exhibits anatomical content and a first visual texture; and
generate, via execution of an optimization algorithm, a second medical image based on the first medical image, wherein the second medical image exhibits the anatomical content and a second visual texture that is different from the first visual texture, and wherein the optimization algorithm is based on feature maps extracted from a pre-trained deep learning neural network that has been configured to perform an inferencing task on medical images exhibiting the second visual texture, wherein the pre-trained deep learning neural network comprises at least one shallow layer and at least one deep layer, and wherein executing the optimization algorithm comprises:

executing the pre-trained deep learning neural network on a representative medical image that exhibits the second visual texture, wherein the pre-trained deep learning neural network produces, based on the representative medical image, at least one first shallow feature map via the at least one shallow layer, and at least one first deep feature map via the at least one deep layer; and
iteratively performs until the second medical image is generated:
wherein a first iteration comprises:
executing the pre-trained deep learning neural network on the first medical image that exhibits the first visual texture, wherein the pre-trained deep learning neural network produces, based on the first medical image, at least one second shallow feature map via the at least one shallow layer, and at least one second deep feature map via the at least one deep layer, and
generating an updated first medical image based on at least one first error between the at least one first shallow feature map; and the at least one second shallow feature map;
wherein subsequent iterations to the first iteration comprise:
executing, during a current iteration of the subsequent iterations, the pre-trained deep learning neural network on the updated first medical image from an immediately preceding iteration to the current iteration, wherein the pre-trained deep learning neural network produces, based on the updated first medical image from the immediately preceding iteration, at least one third deep feature map via the at least one deep layer, and at least one third shallow feature map via the at least one shallow layer,
generating the updated first medical image for the current iteration based on at least one second error between the at least one first shallow feature map and the at least one third shallow feature map, and further based on at least one third error between the at least one second deep feature map and the at least one third deep feature map,
in response to an objective function associated with the at least one second error and the at least one third error satisfying a defined criterion, using the updated first medical image for the current iteration as the second medical image.

16. The computer program product of claim 15, wherein generating the updated first medical image for the current iteration comprises updating at least one of pixel values or voxel values of the updated first medical image from the immediately preceding iteration based on the at least one second error and the at least one third error.

17. The computer program product of claim 15, wherein the optimization algorithm comprises a stochastic gradient descent algorithm or a Broyden-Fletcher-Goldfarb-Shanno algorithm.

18. The computer program product of claim 15, wherein the at least one shallow layer is associated with processing visual textures.

19. The computer program product of claim 15, wherein:
the first visual texture corresponds to a first medical imaging modality, and the second visual texture corresponds to a second medical imaging modality that is different from the first medical imaging modality; or the first visual texture corresponds to first settings of the first medical imaging modality, and the second visual texture corresponds to second settings of the first medical imaging modality that are different from the first settings.

20. The computer program product of claim 15, wherein the at least one deep layer is associated with processing anatomical contents.

\* \* \* \* \*